(12) United States Patent
Turner et al.

(10) Patent No.: US 8,318,793 B2
(45) Date of Patent: Nov. 27, 2012

(54) HETEROCYCLIC COMPOUNDS AND THEIR USE AS GLYCOGEN SYNTHASE KINASE-3 INHIBITORS

(75) Inventors: Sean Colm Turner, Ludwigshafen (DE); Margaretha Henrica Maria Bakker, Ludwigshafen (DE); Wilfried Hornberger, Ludwigshafen (DE); Falko Ernst Wolter, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 157 days.

(21) Appl. No.: 12/748,875

(22) Filed: Mar. 29, 2010

(65) Prior Publication Data
US 2011/0003810 A1    Jan. 6, 2011

Related U.S. Application Data

(60) Provisional application No. 61/163,940, filed on Mar. 27, 2009.

(51) Int. Cl.
*A61K 31/40* (2006.01)
*C07D 209/34* (2006.01)
*C07D 295/00* (2006.01)

(52) U.S. Cl. ........ 514/412; 514/418; 514/421; 548/486; 548/518

(58) Field of Classification Search .................. 514/412, 514/418, 421; 548/486, 518
See application file for complete search history.

(56) References Cited

FOREIGN PATENT DOCUMENTS

| WO | 03053330 A2 | 7/2003 |
| WO | 03053444 A1 | 7/2003 |
| WO | 03055492 A1 | 7/2003 |
| WO | 2003055877 A1 | 7/2003 |
| WO | 2003082853 A1 | 10/2003 |
| WO | 2007089192 A1 | 8/2007 |
| WO | 2007120102 A1 | 10/2007 |
| WO | 2008130312 A1 | 10/2008 |

OTHER PUBLICATIONS

King, F.D. (Ed.), "Bioisosteres, conformational restriction and pro-drugs—case history: an example of a conformational restriction approach," Medical Chemistry: Principles and Practice, 1994, Chapter 14, 206-209.*
Barth, B. et al., Antiviral chemistry & Chemotherapy 7(6), 1996, 300-312.
Heinisch, G. et al., Arch. Pharm. Med. Chem. 2000, 333, 231-240.
Ott, I. et al., J. Med. Chem. 2004, 47, 4627-4630.
Heinisch, G. et al., Arch. Pharm. Med. Chem. 1997, 330, 29-34.

* cited by examiner

*Primary Examiner* — Paul Zarek
(74) *Attorney, Agent, or Firm* — Lisa V. Mueller; Michael Best & Friedrich LLP

(57) ABSTRACT

The present invention relates to novel heterocyclic compounds which are useful for inhibiting glycogen synthase kinase 3 (GSK-3), methods of making the compounds, compositions containing the compounds, and methods of treatment using the compounds.

19 Claims, No Drawings

HETEROCYCLIC COMPOUNDS AND THEIR USE AS GLYCOGEN SYNTHASE KINASE-3 INHIBITORS

CROSS REFERENCE

This claims priority to U.S. Provisional Application No. 61/163,940, filed Mar. 27, 2009, the contents of all of which are incorporated herein by reference.

TECHNICAL FIELD

The present invention relates to novel heterocyclic compounds which are useful for inhibiting glycogen synthase kinase 3 (GSK-3), methods of making the compounds, compositions containing the compounds, and methods of treatment using the compounds.

BACKGROUND OF THE INVENTION

Glycogen synthase kinase-3 (GSK-3) is a serine/threonine kinase encoded by two isoforms, GSK-3α and GSK-3β, with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammalians thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognised that GSK-3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that compounds which modulate the GSK-3β activity may find application in the treatment of the neuropathological consequences and the cognitive and attention deficits associated with Alzheimer's disease, as well as other acute and chronic neurodegenerative diseases. These include, but are not limited to: Parkinson's disease, tauopathies (e.g. frontotemporoparietal dementia, corticobasal degeneration, Pick's disease, progressive supranuclear palsy, argyophilic grain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma.

GSK-3β may further have utility in the treatment of inflammatory diseases, such as rheumatoid arthritis and osteoarthritis.

GSK-3β may also have utility in the treatment of other diseases such as: Non-insulin dependent diabetes and obesity; osteoporosis; manic depressive illness; schizophrenia; alopecia; cancers such as breast cancer, non-small cell lung carcinoma, thyroid cancer, T or B-cell leukemia and several virus-induced tumors.

A review on GSK-3, its functions, its therapeutic potential and its possible inhibitors is given in "Glycogen Synthase Kinase 3 (GSK-3) and its inhibitors: Drug Discovery and Developments" by A. Martinez et al. (editors), John Wiley and Sons, 2006.

B. Barth et al. (Antiviral Chemistry & Chemotherapy 7 (6), 1996, 300-312) describe 6-alkyl substituted pyridazino[3,4-b][1,5]benzoxazepin-5-ones which are useful as inhibitors of HIV-1 reverse transcriptase. They also describe several pyridazino[3,4-b][1,5]benzoxazepin-5(6H)-ones being unsubstituted at the nitrogen as intermediates, namely pyridazino-[3,4-b][1,5]benzoxazepin-5(6H)-one, 3-chloropyridazinobenzo[3,4-b][1,5]benzoxazepin-5(6H)-one, 3-chloro-8-trifluoromethylpyridazino[3,4-b][1,5]-benzoxazepin-5(6H)-one, 3-chloro-9-methylpyridazino[3,4-b][1,5]benzoxazepin-5(6H)-one, 3-chloro-9-methylpyridazino[3,4-b][1,5]benzoxazepin-5(6H)-one, 3-chloro-8-methoxypyridazino[3,4-b][1,5]benzoxazepin-5(6H)-one and 3-chloro-8,10-dimethylpyridazinobenzo[3,4-b][1,5]benzoxazepin-5(6H)-one.

G. Heinisch et al. (Arch. Pharm. Pharm. Med. Chem. 2000, 333, 231-240) describe pyridazinobenzo[3,4-b][1,5]benzoxazepin-5(6H)-ones being unsubstituted at the nitrogen as intermediates in the synthesis of the corresponding N-alkyl derivatives, namely 3-chloropyridazinobenzo[3,4-b][1,5]benzoxazepin-5(6H)-one, 3,8-dichloropyridazino[3,4-b][1,5]benzoxazepin-5(6H)-one, 3-chloro-8-methylpyridazino[3,4-b][1,5]benzoxazepin-5(6H)-one and 3-chloro-9-methylpyridazino[3,4-b][1,5]benzoxazepin-5(6H)-one.

I. Ott et al. (J. Med. Chem. 2004, 47, 4627-4630) describe 6-alkyl substituted pyridazinobenzo[3,4-b][1,5]benzoxazepin-5-ones which are useful as Multidrug-Resistance Modulating agents in tumor therapy. They also describe several pyridazinobenzo[3,4-b][1,5]benzoxazepin-5(6H)-ones being unsubstituted at the nitrogen as intermediates, e.g. 3-chloro-9-trifluoromethylpyridazino[3,4-b][1,5]-benzoxazepin-5(6H)-one.

G. Heinisch et al. (Arch. Pharm. Pharm. Med. Chem. 1997, 330, S. 29-34 and Heterocycles 1997, 45, 673-682) describe inter alia 3-chloro-8-nitro-11-propylpyridazino[3,4-b][1,5]benzodiazipin-5-one.

WO 03/053330 describes 2-oxindoles substituted in the 3-position with a bicyclic hetaryl group and their use for treating conditions related to glycogen synthase kinase-3. WO 03/053444 describes substituted quinazolines and their use for treating conditions related to glycogen synthase kinase-3. WO 03/055492 and WO 03/055877 describe 3-quinazolin-substituted 2-oxindoles and their use for treating conditions related to glycogen synthase kinase-3. WO 03/082853 describes substituted 2-oxindoles substituted in the 3-position with a monocyclic hetaryl group and their use for treating conditions related to glycogen synthase kinase-3. WO 2007/120102 describes 3-[5-(morpholin-4-ylmethyl)-pyridin-2-yl]1H-indol-5-carbonitrile, 2-hydroxy-3-[5-(morpholin-4-ylmethyl)-pyridin-2-yl]1H-indol-5-carbonitrile and their N-oxides and their use for treating conditions related to glycogen synthase kinase-3. WO 2007/089192 describes the use of 3-[5-(morpholin-4-ylmethyl)-pyridin-2-yl]1H-indol-5-carbonitrile for the treatment of bone-related conditions. WO 2008/130312 describes a process for preparing 2-hydroxy-3-[5-(morpholin-4-ylmethyl)-pyridin-2-yl]1H-indol-5-carbonitrile.

SUMMARY OF THE INVENTION

The object of the present invention is to provide compounds which modulate the GSK-3β activity, in particular compounds which have an inhibitory activity on GSK-3β and which thus are useful as an active ingredient of a composition for preventive and/or therapeutic treatment of a disease caused by abnormal GSK-3β activity, especially of neurodegenerative and/or inflammatory diseases. More specifically, the goal is to provide novel compounds useful as an active ingredient of a composition that enables prevention and/or treatment of neurodegenerative diseases such as Alzheimer's disease.

It was surprisingly found that the problem is solved by providing a heterocyclic compound of the general formulae IA and IB

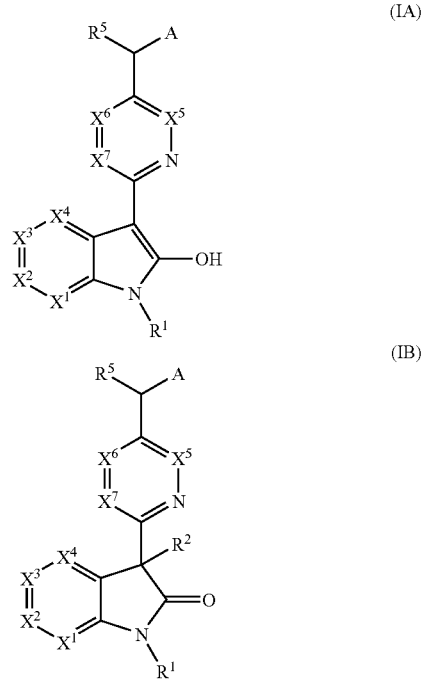

the stereoisomers, N-oxides, prodrugs, tautomers and/or physiologically tolerated acid addition salts thereof, wherein
A is a 3-, 4-, 5-, 6- or 7-membered monocyclic saturated N-bound heterocyclic ring containing one nitrogen atom and optionally 1, 2 or 3 further heteroatoms or heteroatom-containing groups selected from N, O, S, SO and $SO_2$ as ring members and optionally carrying 1, 2, 3 or 4 substituents $R^6$; or is a 6-, 7-, 8-, 9-, 10-, 11-, 12-, 13- or 14-membered bicyclic or tricyclic saturated N-bound heterocyclic ring containing one nitrogen atom and optionally 1, 2 or 3 further heteroatoms or heteroatom-containing groups selected from N, O, S, SO and $SO_2$ as ring members and optionally carrying 1, 2, 3 or 4 substituents $R^6$;
$X^1$, $X^2$, $X^3$ and $X^4$ are independently of each other selected from the group consisting of $CR^3$ and N;
  with the proviso that at least one of $X^1$, $X^2$, $X^3$ and $X^4$ is N in case that A is a mono-cyclic ring;
$X^5$, $X^6$ and $X^7$ are independently of each other selected from the group consisting of $CR^4$ and N;
  with the proviso that at most one of $X^5$, $X^6$ and $X^7$ is N;
$R^1$ is hydrogen or a hydrolysable group;
$R^2$ is hydrogen, OH or F;
each $R^3$ is independently selected from the group consisting of hydrogen, CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_5$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^7$ and wherein Ar may also be bonded via a $CH_2$ group;
each $R^4$ is independently selected from the group consisting of hydrogen, CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^7$ and wherein Ar may also be bonded via a $CH_2$ group; or
  in case $X^6$ and $X^7$ are both $CR^4$, then the two radicals $R^4$ of these groups $X^5$ and $X^7$, together with the carbon atoms to which they are bound, may also form together a phenyl ring;
$R^5$ is hydrogen; or
  in case $X^6$ is $CR^4$, then $R^4$ of this group $X^6$ and $R^5$, together with the carbon atoms to which they are bound, may also form together a phenyl ring;
each $R^6$ is independently selected from the group consisting of $C_1$-$C_4$-alkyl and $C_1$-$C_4$-haloalkyl;
each $R^7$ is independently selected from the group consisting of halogen, CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, a phenyl group and an aromatic 5- or 6-membered C-bound heteroaromatic radical comprising one nitrogen atom and optionally 1, 2 or 3 further heteroatoms independently selected from O, S and N as ring members, wherein phenyl and the heteroaromatic radical are, independently of each other, unsubstituted or substituted by 1, 2, 3 or 4 radicals selected from halogen, cyano, $C_1$-$C_4$-alkyl, $C_1$-$C_4$-haloalkyl, $C_1$-$C_4$-alkoxy and $C_1$-$C_4$-haloalkoxy; and $R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-haloalkylcarbonyl; or $R^a$ and $R^b$ form, together with the nitrogen atom to which they are bonded, a 3-, 4-, 5-, 6- or 7-membered saturated or unsaturated non-aromatic or non-aromatic N-bound heterocyclic ring, which may contain 1 further heteroatom or heteroatom-containing group selected from N, O, S, SO and $SO_2$ as a ring member.

Thus, the present invention relates to compounds of the formulae IA and IB as defined herein and in the claims, to the stereoisomers, tautomers, prodrugs and/or physiologically tolerated acid addition salts thereof.

According to a further aspect, the present invention relates to a pharmaceutical composition comprising at least one compound of the formula IA and/or IB as defined herein, a stereoisomer, a tautomer, a prodrug and/or a physiologically tolerated acid addition salt thereof, optionally together with at least one physiologically acceptable carrier and/or auxiliary substance.

According to a further aspect, the present invention relates to the use of at least one compound of the formula IA and/or IB as defined herein, the stereoisomers, tautomers, prodrugs and/or physiologically tolerated acid addition salts thereof, for the preparation of a medicament for the treatment of a medical disorder susceptible to treatment with a compound that modulates glycogen synthase kinase 3β activity.

According to a further aspect, the present invention relates to a method for treating a medical disorder susceptible to treatment with a compound that modulates glycogen synthase kinase 3β activity, said method comprising administering an effective amount of at least one compound of the formula IA and/or IB as defined herein, a stereoisomer, a tautomer, a prodrug and/or a physiologically tolerated acid addition salt thereof, to a subject in need thereof.

DETAILED DESCRIPTION OF THE INVENTION

Provided the compounds of the formulae IA and IB of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formulae IA and IB and/or of their salts.

In case $R^2$ in compound IB is hydrogen, this compound IB is a tautomer of the respective compound IA wherein the remaining variables have the same meaning.

It is likewise possible to use physiologically tolerated salts of the compounds of the formulae IA and/or IB, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluene-sulfonic acid, oxalic acid, maleic acid, fumaric acid, lactic acid, tartaric acid, adipic acid and benzoic acid. Other utilizable acids are described in Fortschritte der Arzneimittelfor-schung [Advances in drug research], Volume 10, pages 224 et seq., Birkhäiser Verlag, Basel and Stuttgart, 1966.

In the terms of the present invention, "prodrugs" are compounds which are metabolized in vivo to give the compounds of the invention of formulae IA or IB. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula IA or IB wherein an external nitrogen atom, for example a secondary nitrogen ring atom of the heterocyclic group A or a nitrogen atom of a primary or secondary amino group being a substituent $R^3$, $R^4$ and/or $R^7$ (=at least one of $R^3$, $R^4$ and $R^7$ is $NR^aR^b$, wherein at least one of $R^a$ and $R^b$ is H), forms an amide/peptide bond in that this nitrogen atom is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an aminoacid group bonded via CO, e.g. glycine, alanine, serine, phenylalanine and the like bonded via CO. Suitable prodrugs are furthermore alkylcarbonyloxyalkylcarbamates, wherein said nitrogen atom carries a group —C(=O)—O—CHR$^x$—O—C(=O)—R$^y$, wherein $R^x$ and $R^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322. These groups can be removed under metabolic conditions and result in compounds I wherein said nitrogen atom carries a hydrogen atom instead. Also, $R^1$ may be chosen so as to be hydrolysable under metabolic conditions and thus to be one of the above-listed groups (i.e. a $C_1$-$C_4$-alkylcarbonyl group, an aminoacid group bonded via CO or a group —C(=O)—O—CHR$^x$—O—C(=O)—R$^y$).

The compounds of formulae IA or IB may also be present in the form of the respective tautomers. Apart the tautomery already mentioned above of formulae IA and IB, where in formula IB $R^2$ is H, tautomery may also be present in compounds IA and IB wherein $R^3$ is OH and this substituent is bonded to a carbon atom which is in α-position to a nitrogen ring atom. This results for example in following tautomeric formulae (the examples are only given for formula IA, but are analogous for formula IB):

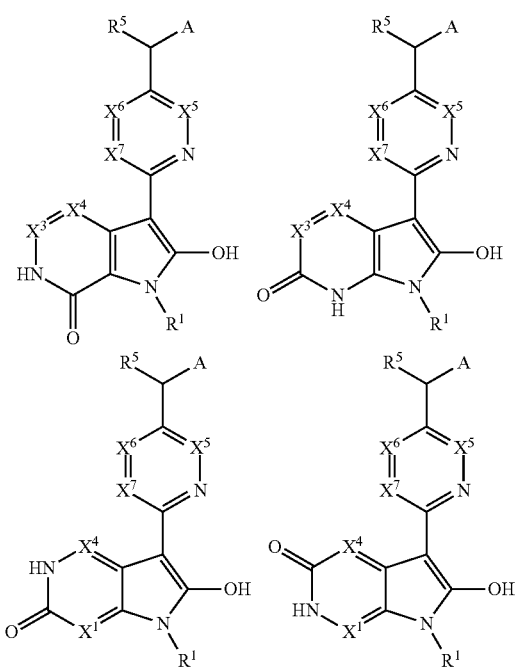

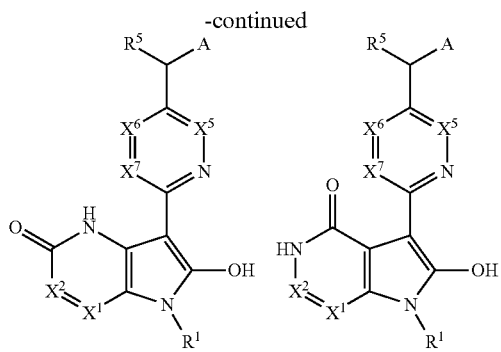

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_2$-Alkyl is methyl or ethyl; $C_1$-$C_3$-alkyl is additionally n-propyl or isopropyl.

$C_1$-$C_4$-Alkyl is a straight-chain or branched alkyl group having from 1 to 4 carbon atoms. Examples are methyl, ethyl, n-propyl, isopropyl, n-butyl, 2-butyl (sec-butyl), isobutyl and tent-butyl.

$C_1$-$C_6$-Alkyl is a straight-chain or branched alkyl group having from 1 to 6 carbon atoms. Examples include the residues mentioned above for $C_1$-$C_4$-alkyl and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_2$-Haloalkyl is an alkyl group having 1 or 2 carbon atoms (as mentioned above), where at least one of the hydrogen atoms, e.g. 1, 2, 3, 4 or 5 hydrogen atoms in these groups are replaced by halogen atoms as mentioned above, such as chloromethyl, dichloromethyl, trichloromethyl, fluoromethyl, difluoromethyl, trifluoromethyl, bromomethyl, chlorofluoromethyl, dichlorofluoromethyl, chlorodifluoromethyl, 1-chloroethyl, 1-bromoethyl, 1-fluoroethyl, 2-chloroethyl, 2-bromoethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

$C_1$-$C_4$-Haloalkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by halogen atoms as mentioned above. Examples are, apart those listed above for $C_1$-$C_2$-haloalkyl, 1-chloropropyl, 1-bromopropyl, 1-fluoropropyl, 2-chloropropyl, 2-bromopropyl, 2-fluoropropyl, 3-chloropropyl, 3-bromopropyl, 3-fluoropropyl, 1,1-dichloropropyl, 1,1-difluoropropyl, 2,2-dichloropropyl, 2,2-difluoropropyl, 2,3-dichloropropyl, 2,3-difluoropropyl, 1,3-dichloropropyl, 1,3-difluoropropyl, 3,3-dichloropropyl, 3,3-difluoropropyl, 1,1,2-trichloropropyl, 1,1,2-trifluoropropyl, 1,2,2-trichloropropyl, 1,2,2-trifluoropropyl, 1,2,3-trichloropropyl, 1,2,3-trifluoropropyl, 2,2,3-trichloropropyl, 2,2,3-trifluoropropyl, 3,3,3-trichloropropyl, 3,3,3-trifluoropropyl, 1,1,1-trifluoroprop-2-yl, 1-chlorobutyl, 1-bromobutyl, 1-fluorobutyl, 2-chlorobutyl, 2-bromobutyl, 2-fluorobutyl, 3-chlorobutyl, 3-bromobutyl, 3-fluorobutyl, 4-chlorobutyl, 4-bromobutyl, 4-fluorobutyl, and the like.

$C_1$-$C_6$-Haloalkyl is a straight-chain or branched alkyl group having 1 to 6 carbon atoms (as mentioned above), where at least one of the hydrogen atoms in these groups is replaced by halogen atoms as mentioned above. Examples are, apart those listed above for $C_1$-$C_4$-haloalkyl, chloropentyl, bromopentyl, fluoropentyl, chlorohexyl, bromohexyl, fluorohexyl, and the like.

$C_1$-$C_2$-Fluoroalkyl (=fluorinated $C_1$-$C_2$-alkyl) is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl.

$C_1$-$C_4$-Fluoroalkyl (=fluorinated $C_1$-$C_4$-alkyl) is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_2$-fluoroalkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like.

$C_1$-$C_6$-Fluoroalkyl (=fluorinated $C_1$-$C_6$-alkyl) is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_4$-fluoroalkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 65-fluorohexyl, (R)-6-fluorohexyl, (S)-6-fluorohexyl, and the like.

$C_1$-$C_4$-Alkoxy is a straight-chain or branched alkyl group having from 1 to 4 carbon atoms, which is bound to the remainder of the molecule via an oxygen atom. Examples include methoxy, ethoxy, n-propoxy, isopropoxy, n-butoxy, 2-butoxy, isobutoxy and tert-butoxy.

$C_1$-$C_5$-Alkoxy is a straight-chain or branched alkyl group having from 1 to 6 carbon atoms, which is bound to the remainder of the molecule via an oxygen atom. Examples include, apart those listed above for $C_1$-$C_4$-alkoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methyl pentyloxy, 3-methyl pentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy (which is also termed $C_1$-$C_6$-haloalkoxy), in particular fluorinated $C_1$-$C_6$-alkoxy (also termed $C_1$-$C_6$-fluoroalkoxy) is a straight-chain or branched alkoxy group having from 1 to 6, in particular 1 to 4 carbon atoms (=fluorinated $C_1$-$C_4$-alkoxy), wherein at least one, e.g. 1, 2, 3, 4 or all of the hydrogen atoms are replaced by a halogen atoms, in particular fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_4$-Alkylcarbonyl is a straight-chain or branched alkyl group having from 1 to 4 carbon atoms), which is bound to the remainder of the molecule via a carbonyl group (CO), such as in acetyl, propionyl, isopropylcarbonyl, butylcarbonyl, sec-butylcarbonyl, isobutylcarbonyl, and tert-butylcarbonyl.

$C_1$-$C_6$-Alkylcarbonyl is a straight-chain or branched alkyl group having from 1 to 6 carbon atoms, which is bound to the remainder of the molecule via a carbonyl group (CO). Examples include, apart those listed above for $C_1$-$C_4$-alkylcarbonyl, pentylcarbonyl, hexylcarbonyl and the constitutional isomers thereof.

$C_1$-$C_4$-Haloalkylcarbonyl is a straight-chain or branched haloalkyl group having from 1 to 4 carbon atoms as defined above, which is bound to the remainder of the molecule via a carbonyl group (CO)

$C_1$-$C_6$-Haloalkylcarbonyl is a straight-chain or branched haloalkyl group having from 1 to 6 carbon atoms as defined above, which is bound to the remainder of the molecule via a carbonyl group (CO)

$C_1$-$C_4$-fluoroalkylcarbonyl is a straight-chain or branched fluoroalkyl group having from 1 to 4 carbon atoms as defined above, which is bound to the remainder of the molecule via a carbonyl group (CO)

$C_1$-$C_6$-fluoroalkylcarbonyl is a straight-chain or branched fluoroalkyl group having from 1 to 6 carbon atoms as defined above, which is bound to the remainder of the molecule via a carbonyl group (CO)

$C_1$-$C_6$-Alkoxycarbonyl is a straight-chain or branched alkoxy group having from 1 to 6, especially 1 to 4 carbon atoms (=$C_1$-$C_4$-alkoxycarbonyl), in particular 1 to 3 carbon atoms (=$C_1$-$C_3$-alkoxycarbonyl), which is bound to the remainder of the molecule via a carbonyl group (CO), such as in methoxycarbonyl, ethoxycarbonyl, propyloxycarbonyl, and isopropyloxycarbonyl.

$C_1$-$C_6$-Haloalkoxycarbonyl is a straight-chain or branched haloalkoxy group having from 1 to 6, especially 1 to 4 carbon atoms (=$C_1$-$C_4$-haloalkoxycarbonyl), in particular 1 to 3 carbon atoms (=$C_1$-$C_3$-haloalkoxycarbonyl) as defined above, which is bound to the remainder of the molecule via a carbonyl group (CO).

$C_1$-$C_6$-Fluoroalkoxycarbonyl is a straight-chain or branched fluorooalkoxy group having from 1 to 6, especially 1 to 4 carbon atoms (=$C_1$-$C_4$-fluoroalkoxycarbonyl), in particular 1 to 3 carbon atoms (=$C_1$-$C_3$-fluoroalkoxycarbonyl) as defined above, which is bound to the remainder of the molecule via a carbonyl group (CO).

$C_3$-$C_6$-Cycloalkyl is a cycloaliphatic radical having from 3 to 6 C atoms, such as cyclopropyl, cyclobutyl, cyclopentyl and cyclohexyl. $C_3$-$C_4$-cycloalkyl is a cycloaliphatic radical having from 3 to 4 C atoms, such as cyclopropyl and cyclobutyl.

$C_3$-$C_7$-Cycloalkyl is a cycloaliphatic radical having from 3 to 7 C atoms, such as cyclopropyl, cyclobutyl, cyclopentyl, cyclohexyl and cycloheptyl.

$C_3$-$C_6$-Halocycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a halogen atoms, preferably by fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_7$Halocycloalkyl is a cycloaliphatic radical having from 3 to 7 C atoms, such as cyclopropyl, cyclobutyl, cyclopentyl, cyclohexyl and cycloheptyl, wherein at least one, e.g. 1, 2, 3, 4 or all of the hydrogen atoms are replaced by a halogen atoms, preferably by fluorine atoms. Examples include, apart those listed above for $C_3$-$C_6$-fluorocycloalkyl, 1-fluorocycloheptyl, 2-fluorocycloheptyl, 3-fluorocycloheptyl, 4-fluorocycloheptyl, 1,2-difluorocycloheptyl, 1,3-difluorocycloheptyl, 1,4-difluorocycloheptyl, 2,2-difluorocycloheptyl, 2,3-difluorocycloheptyl, 2,4-difluorocycloheptyl, 2,5-difluorocycloheptyl, 2,6-difluorocycloheptyl, 2,7-difluorocycloheptyl, 3,3-difluorocycloheptyl, 3,4-difluorocycloheptyl, 3,5-difluorocycloheptyl, 3,6-difluorocycloheptyl, 4,4-difluorocycloheptyl, 4,5-difluorocycloheptyl, and the like.

$C_2$-$C_4$-Alkenyl is a singly unsaturated hydrocarbon radical having 2, 3 or 4 C-atoms, e.g. vinyl, allyl (2-propen-1-yl), 1-propen-1-yl, 2-propen-2-yl, methallyl(2-methylprop-2-en-1-yl) and the like.

$C_2$-$C_4$-Haloalkenyl is a singly unsaturated hydrocarbon radical having 2, 3 or 4 C-atoms, wherein at least one, e.g. 1, 2, 3, 4 or all of the hydrogen atoms are replaced by halogen atoms, preferably by fluorine atoms such as in 1-fluorovinyl, 2-fluorovinyl, 2,2-fluorovinyl, 3,3,3-fluoropropenyl, 1,1-difluoro-2-propenyl, 1-fluoro-2-propenyl and the like.

Examples for 5- or 6-membered N- or C-bound heteroaromatic radicals comprising one nitrogen atom and optionally 1, 2 or 3 further heteroatoms independently selected from O, S and N as ring members are pyrrol-1-yl, pyrrol-2-yl, pyrrol-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]-1H-triazol-1-yl, [1,2,3]-1H-triazol-4-yl, [1,2,3]-1H-triazol-5-yl, [1,2,3]-2H-triazol-2-yl, [1,2,3]-2H-triazol-4-yl, [1,2,3]-2H-triazol-5-yl, [1,2,4]-1H-triazol-1-yl, [1,2,4]-1H-triazol-3-yl, [1,2,4]-1H-triazol-5-yl, [1,2,4]-4H-triazol-4-yl, oxadiazolyl, thiadiazolyl, [1,2,3,4]-1H-tetrazol-1-yl, [1,2,3,4]-1H-tetrazol-5-yl, [1,2,3,4]-2H-tetrazol-2-yl, [1,2,3,4]-2H-tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and triazin-2-yl.

Examples for N-bound 3-, 4-, 5-, 6- or 7-membered saturated or unsaturated aromatic or non-aromatic N-heterocyclic rings, which may contain 1 further heteroatom or heteroatom-containing group selected from the group consisting of O, S, SO, SO$_2$ and N as a ring member, are aziridin-1-yl, azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-1-yl, [1,2,3]-triazolidin-1-yl, [1,2,3]-triazolidin-2-yl, [1,2,4]-triazolidin-1-yl, [1,2,4]-triazolidin-4-yl, piperidin-1-yl, piperazin-1-yl, morpholin-4-yl, thiomorpholin-1-yl, 1-oxohiomorpholin-1-yl, 1,1-dioxothiomorpholin-1-yl, azepan-1-yl, azirin-1-yl, azetin-1-yl, pyrrolin-1-yl, pyrazolin-1-yl, imidazolin-1-yl, oxazolin-3-yl, isoxazolin-2-yl, thiazolin-3-yl, isothiazolin-1-yl, 1,2-dihydropyridin-1-yl, 1,2,3,4-tetrahydropyridin-1-yl, 1,2,5,6-tetrahydropyridin-1-yl, 1,2-dihydropyridazin, 1,6-dihydropyridazin, 1,2,3,4-tetrahydropyridazin-1-yl, 1,2,5,6-tetrahydropyridazin-1-yl, 1,2-dihydropyrimidin, 1,6-dihydropyrimidin, 1,2,3,4-tetrahydropyrimidin-1-yl, 1,2,5,6-tetrahydropyrimidin-1-yl, 1,2-dihydropyrazin-1-yl, 1,2,3,4-tetrahydropyrazin-1-yl, 1,2,5,6-tetrahydropyrazin-1-yl, pyrrol-1-yl, pyrazol-1-yl, imidazol-1-yl, [1,2,3]-1H-triazol-1-yl, [1,2,3]-2H-triazol-2-yl, [1,2,4]-1H-triazol-1-yl and [1,2,4]-4H-triazol-4-yl.

6-, 7-, 8-, 9-, 10-, 11-, 12-, 13- or 14-membered bicyclic or tricyclic rings are preferably 6-, 7-, 8-, 9-, 10-, 11 or 12-membered bicyclic rings or are 8-, 9-, 10-, 11-, 12-, 13- or 14-membered tricyclic rings.

Examples for N-bound 6-, 7-, 8-, 9-, 10-, 11-, 12-, 13- or 14-membered bicyclic or tricyclic saturated heterocyclic ring containing one nitrogen atom and optionally 1, 2 or 3 further heteroatoms or heteroatom-containing groups selected from N, O, S, SO and SO$_2$ as ring members and optionally carrying 1, 2, 3 or 4 substituents R$^6$ include the radicals of the following formulae:

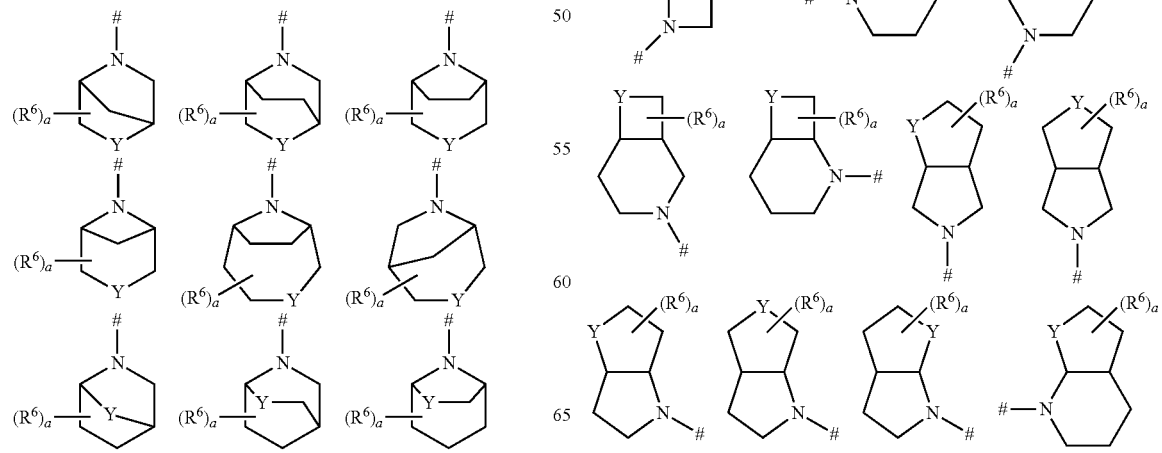

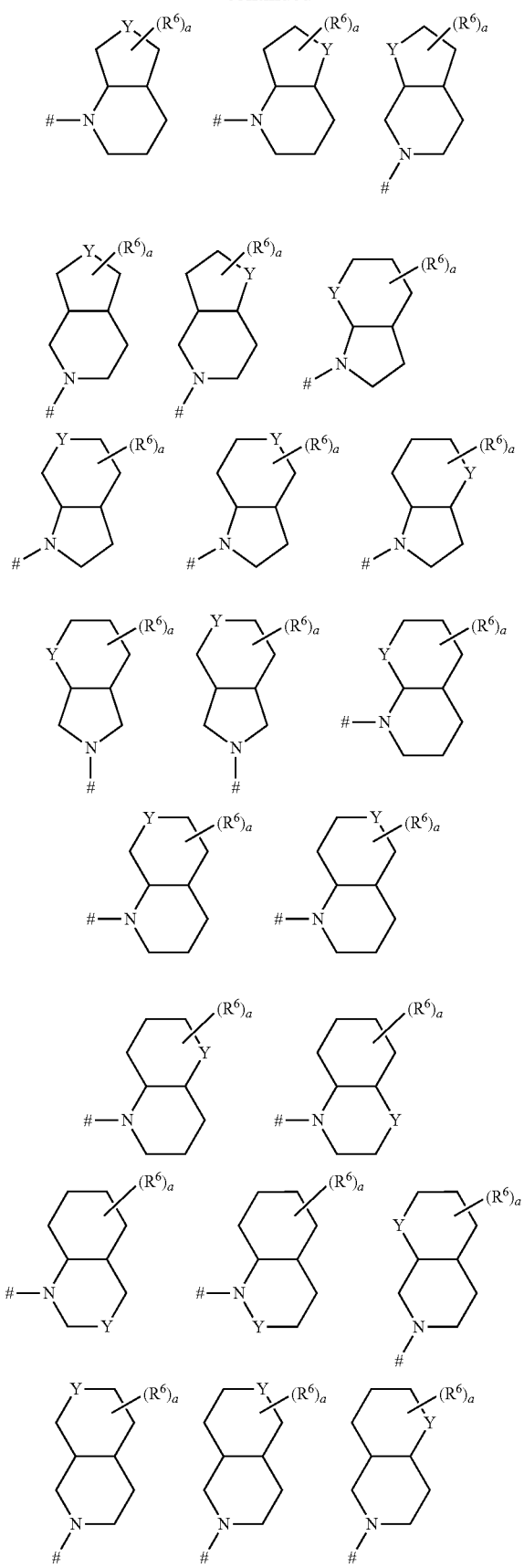
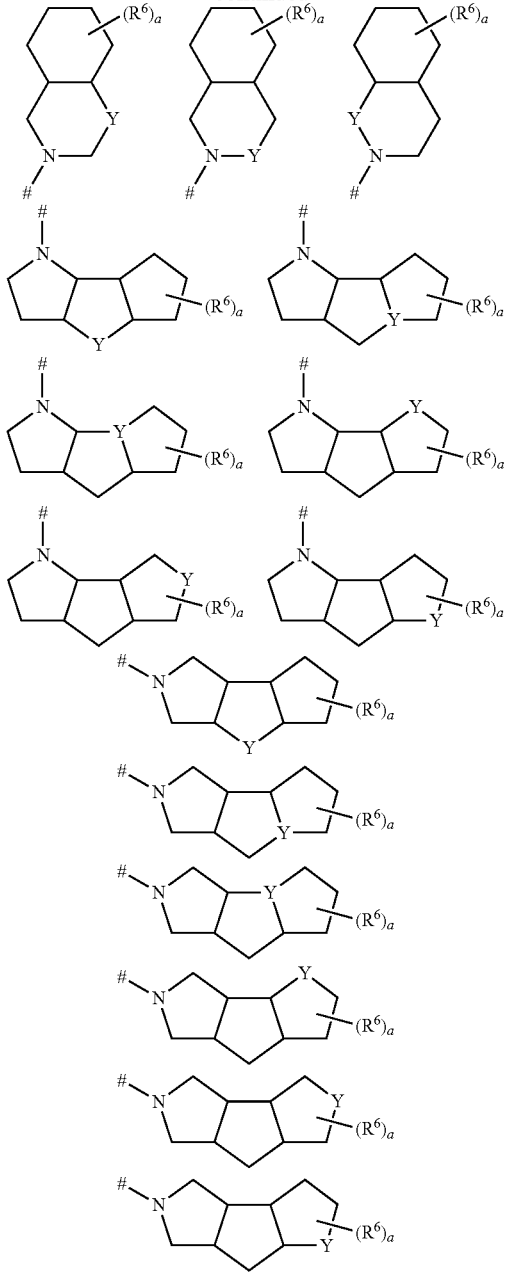

and the like and all stereoisomers thereof, where
Y is $CH_2$, CH (if Y is a bridge atom), NH, N (if Y is part of a double bond or is a bridge atom), O, S, SO or $SO_2$, preferably NH or O,
with the proviso that Y is not O or S if Y is a bridge atom;
$R^6$ has one of the general meanings given above or one of the preferred meanings given below;
a is 0, 1, 2, 3 or 4, preferably 0, 1 or 2 and more preferably 0 or 1; and
# is the attachment point to the remainder of the molecule.

$R^6$ can also be located on a nitrogen atom where it replaces the hydrogen atom. $R^6$ and the attachment point can be located on the same ring or on different rings. $R^6$ can also be bound to a bridge atom. However, $R^6$ and the attachment point are preferably located on different rings and as shown above. Preferably, $R^6$, if present, is bound to a nitrogen atom or to a bridge atom.

If $R^1$ is a hydrolysable group, it is preferably hydrolysable under metabolic conditions. Hydrolysable means that this group, preferably when exposed to metabolic conditions, is converted into hydrogen. Examples for such groups $R^1$ are the groups listed in the above definition of prodrugs, such as $C_1$-$C_4$-alkylcarbonyl, aminoacid groups bonded via CO or a group —C(=O)—O—CHR$^x$—O—C(=O)—R$^y$), but also $C_1$-$C_4$-haloalkylcarbonyl, $C_3$-$C_6$-cycloalkylcarbonyl, $C_1$-$C_4$-alkoxycarbonyl, aryloxycarbonyl, $C_1$-$C_4$-alkylaminocarbonyl and di-($C_1$-$C_4$-alkyl)-aminocarbonyl.

If $X^6$ and $X^7$ are both $CR^4$ and the two radicals $R^4$ of groups $X^6$ and $X^7$ form together with the carbon atoms to which they are bound a phenyl ring, this results in a moiety of the following formula:

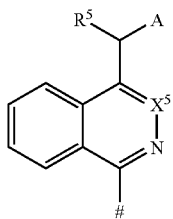

If $X^6$ is $CR^4$ and $R^4$ of this group $X^6$ and $R^5$, together with the carbon atoms to which they are bound, form together a phenyl ring, this results in a moiety of the following formula:

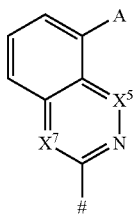

The remarks made above and in the following with respect to preferred aspects of the invention, e.g. to preferred meanings of the variables A, $X^1$, $X^2$, $X^3$, $X^4$, $X^5$, $X^6$, $X^7$, $R^1$, $R^2$, $R^3$, $R^4$, $R^5$, $R^6$, $R^7$, $R^{61}$, $R^a$, $R^b$ of compounds IA and IB, to preferred compounds IA and IB and to preferred embodiments of the method or the use according to the invention, apply in each case on their own or in particular to combinations thereof.

In one embodiment of the invention, A is a monocyclic saturated N-bound heterocyclic ring and at least one of $X^1$, $X^2$, $X^3$ and $X^4$ is N. Preferably, A is a monocyclic saturated N-bound heterocyclic ring and one or two of $X^1$, $X^2$, $X^3$ and $X^4$ is N and the other three or two are $CR^3$. More preferably, A is a monocyclic saturated N-bound heterocyclic ring and one of $X^1$, $X^2$, $X^3$ and $X^4$ is N and the other three are $CR^3$.

Preferably, the monocyclic ring A is selected from aziridin-1-yl, azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, [1,2,3]-triazolidin-1-yl, [1,2,3]-triazolidin-2-yl, [1,2,4]-triazolidin-1-yl, [1,2,4]-triazolidin-4-yl, [1,3,4]-oxazolidin-3-yl, [1,3,4]-thiazolidin-3-yl, piperidin-1-yl, piperazin-1-yl, morpholin-4-yl, thiomorpholin-4-yl, 1-oxothiomorpholin-4-yl, 1,1-dioxothiomorpholin-4-yl and azepan-1-yl. More preferably, the monocyclic ring A is selected from aziridin-1-yl, azetidin-1-yl, pyrrolidin-1-yl, piperidin-1-yl, piperazin-1-yl, morpholin-4-yl and azepan-1-yl. Even more preferably, the monocyclic ring A is selected from pyrrolidin-1-yl, piperidin-1-yl, piperazin-1-yl and morpholin-4-yl. In particular, the monocyclic ring A is morpholin-4-yl.

In another embodiment, A is a bi- or tricyclic saturated N-bound heterocyclic ring. In this case, it is preferred that either all of $X^1$, $X^2$, $X^3$ and $X^4$ are $CR^3$ or one or two of $X^1$, $X^2$, $X^3$ and $X^4$ are N and the other three or two are $CR^3$. More preferably, either all of $X^1$, $X^2$, $X^3$ and $X^4$ are $CR^3$ or one of $X^1$, $X^2$, $X^3$ and $X^4$ is N and the other three are $CR^3$. In particular, all of $X^1$, $X^2$, $X^3$ and $X^4$ are $CR^3$.

Preferably, A is a bicyclic saturated N-bound heterocyclic ring. More preferably, A is a 7-, 8-, 9- or 10-membered bicyclic saturated N-bound heterocyclic ring and optionally carrying 1, 2 or 3 substituents $R^6$ which have one of the general meanings given above or one of the preferred meanings given below (for $R^{61}$). Even more preferably, A is a 7-, 8-, 9- or 10-membered bicyclic saturated N-bound heterocyclic ring containing one nitrogen atom and 1 further heteroatom selected from O and N as ring members and optionally carrying 1, 2 or 3 substituents $R^6$ which have one of the general meanings given above or one of the preferred meanings given below (for $R^{61}$). Preferably, the 7-, 8-, 9- or 10-membered bicyclic saturated N-bound heterocyclic ring containing one nitrogen atom and 1 further heteroatom selected from O and N as ring members is selected from one of the following formulae:

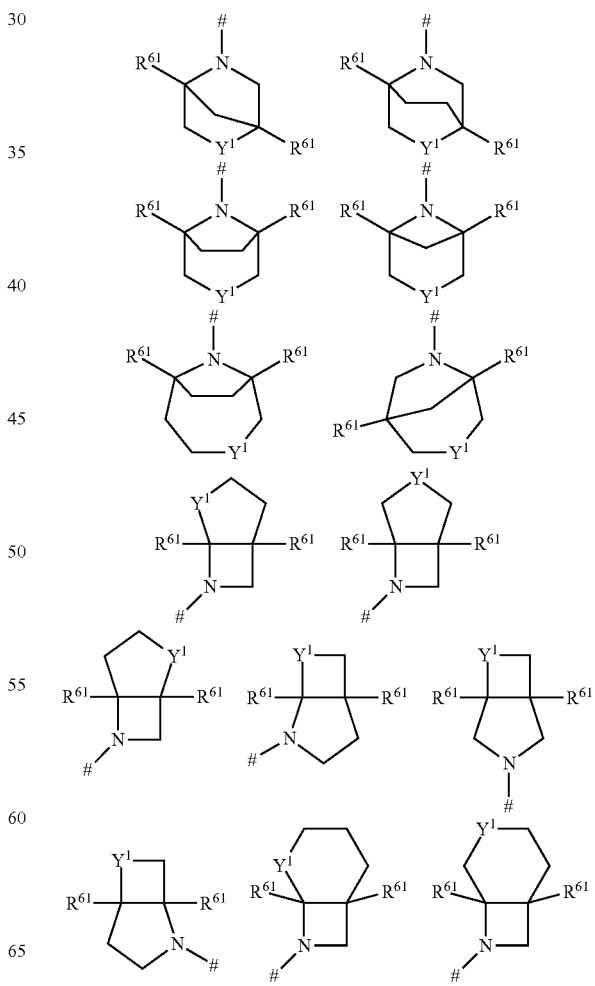

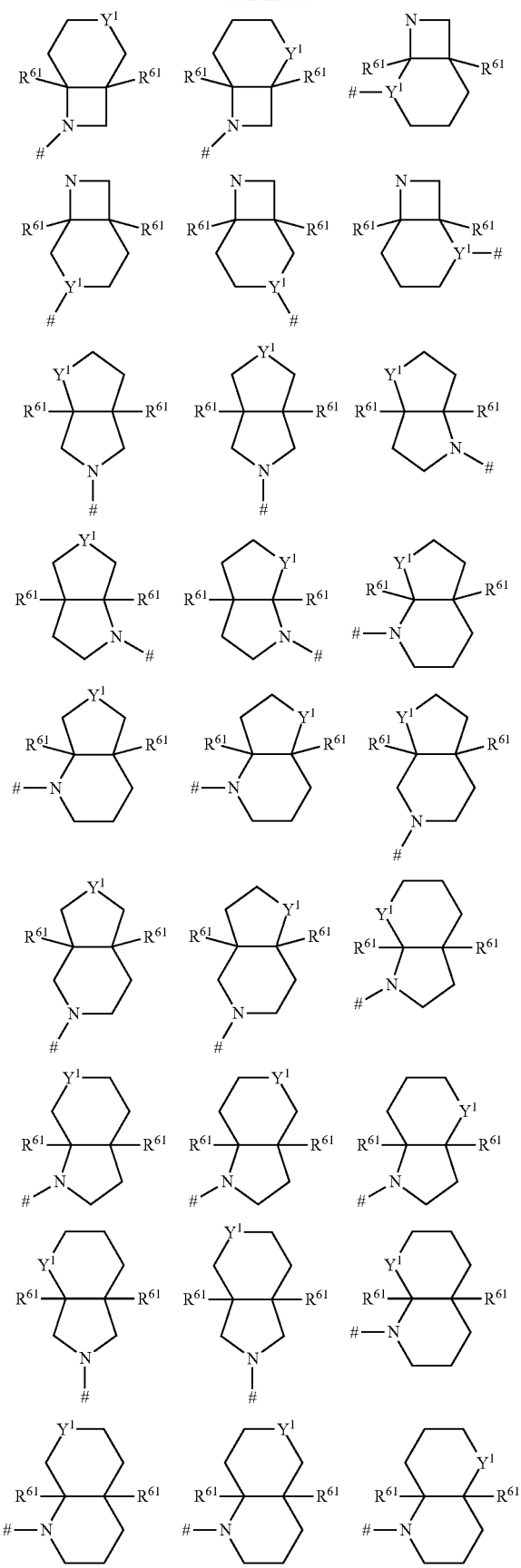
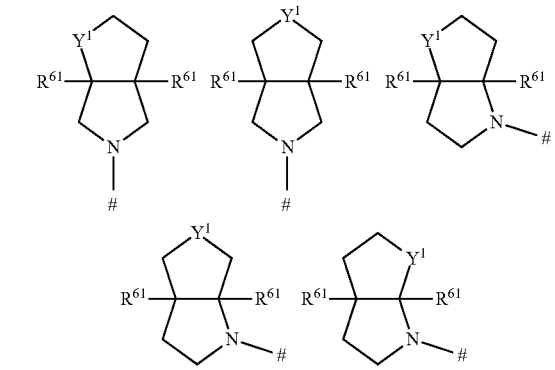

and the stereoisomers thereof;
where
$Y^1$ is O or $NR^{61}$;
each $R^{61}$, independently of its occurrence, is hydrogen or has one of the meanings given above or preferably below for $R^6$ or $R^{61}$; and
# is the attachment point to the remainder of the molecule.

Among these, preference is given to following formulae:

In the above formulae, $R^{61}$ is preferably hydrogen or methyl and more preferably hydrogen.

In one preferred embodiment, $X^5$ is $CR^4$.
In one preferred embodiment, $X^6$ is $CR^4$.
In one preferred embodiment, $X^7$ is $CR^4$.
In a more preferred embodiment, $X^5$, $X^6$ and $X^7$ are $CR^4$.
Preferably, $R^1$ is hydrogen or fluorine and more preferably hydrogen.
Preferably, $R^2$ is hydrogen.
Preferably, each $R^3$ is independently selected from hydrogen, halogen, CN, $C_1$-$C_6$-alkyl, $C_1$-$C_6$-haloalkyl, $C_1$-$C_6$-alkoxy and $C_1$-$C_6$-haloalkoxy. More preferably, each $R^3$ is independently selected from hydrogen, halogen and cyano. Preferably, at most one of $R^3$ is different from hydrogen. In particular, all radicals $R^3$ are hydrogen or one radical $R^3$ is different from hydrogen and is preferably halogen or cyano and the remaining radicals $R^3$ are hydrogen.
Preferably, each $R^4$ is independently selected from hydrogen, halogen, CN, $C_1$-$C_6$-alkyl, $C_1$-$C_6$-haloalkyl, $C_1$-$C_6$-alkoxy and $C_1$-$C_6$-haloalkoxy. More preferably, all radicals $R^4$ are hydrogen.
Preferably, $R^5$ is hydrogen.

Particularly preferred compounds are compounds of formulae IA and IB, the stereoisomers, prodrugs, tautomers and/or physiologically tolerated acid addition salts thereof, wherein
A is morpholin-4-yl;
$X^1$ is N;
$X^2$, $X^3$ and $X^4$ are $CR^3$; preferably CH;
$X^4$, $X^5$ and $X^6$ are CH;
$R^1$ is H;
$R^2$ is H; and
$R^5$ is H.

Alternatively, particularly preferred compounds are compounds of formulae IA and IB, the stereoisomers, prodrugs, tautomers and/or physiologically tolerated acid addition salts thereof, wherein
A is morpholin-4-yl;
$X^2$ is N;
$X^1$, $X^3$ and $X^4$ are $CR^3$; preferably CH; $X^4$, $X^5$ and $X^6$ are CH;
$R^1$ is H;
$R^2$ is H; and
$R^5$ is H.

Alternatively, particularly preferred compounds are compounds of formulae IA and IB, the stereoisomers, prodrugs, tautomers and/or physiologically tolerated acid addition salts thereof, wherein
A is morpholin-4-yl;
$X^3$ is N;
$X^1$, $X^2$ and $X^4$ are $CR^3$; preferably CH;
$X^4$, $X^5$ and $X^6$ are CH;
$R^1$ is H;
$R^2$ is H; and
$R^5$ is H.

Alternatively, particularly preferred compounds are compounds of formulae IA and IB, the stereoisomers, prodrugs, tautomers and/or physiologically tolerated acid addition salts thereof, wherein
A is morpholin-4-yl;
$X^4$ is N;
$X^1$, $X^2$ and $X^3$ are $CR^3$; preferably CH; or $X^1$ and $X^2$ are preferably CH and $X^3$ is $CR^3$ with $R^3$ being halogen or cyano;
$X^4$, $X^5$ and $X^6$ are CH;
$R^1$ is H;
$R^2$ is H; and
$R^5$ is H.

Alternatively, particularly preferred compounds are compounds of formulae IA and IB, the stereoisomers, prodrugs, tautomers and/or physiologically tolerated acid addition salts thereof, wherein
A is

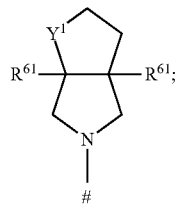

wherein
$Y^1$ is O or $NR^{61}$;
each $R^{61}$ is independently H or methyl, preferably H; and
# is the attachment point to the remainder of the molecule;
$X^1$, $X^2$, $X^3$ and $X^4$ are $CR^3$; where all radicals $R^3$ are H or three radicals $R^3$ are H and one radical $R^3$ is halogen or cyano;
$X^4$, $X^5$ and $X^6$ are CH;
$R^1$ is H;
$R^2$ is H; and
$R^5$ is H.

Alternatively, particularly preferred compounds are compounds of formulae IA and IB the stereoisomers, prodrugs, tautomers and/or physiologically tolerated acid addition salts thereof, wherein
A is

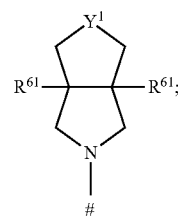

wherein
$Y^1$ is O or $NR^{61}$;
each $R^{61}$ is independently H or methyl, preferably H; and
# is the attachment point to the remainder of the molecule;
$X^1$, $X^2$, $X^3$ and $X^4$ are $CR^3$; where all radicals $R^3$ are H or three radicals $R^3$ are H and one radical $R^3$ is halogen or cyano;
$X^4$, $X^5$ and $X^6$ are CH;
$R^1$ is H;
$R^2$ is H; and
$R^5$ is H.

Alternatively, particularly preferred compounds are compounds of formulae IA and IB the stereoisomers, prodrugs, tautomers and/or physiologically tolerated acid addition salts thereof, wherein
A is

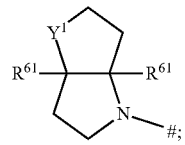

wherein
$Y^1$ is O or $NR^{61}$;
each $R^{61}$ is independently H or methyl, preferably H; and
# is the attachment point to the remainder of the molecule;
X', $X^2$, $X^3$ and $X^4$ are $CR^3$; where all radicals $R^3$ are H or three radicals $R^3$ are H and one radical $R^3$ is halogen or cyano;
$X^4$, $X^5$ and $X^6$ are CH;
$R^1$ is H;
$R^2$ is H; and
$R^5$ is H.

Alternatively, particularly preferred compounds are compounds of formulae IA and IB the stereoisomers, prodrugs, tautomers and/or physiologically tolerated acid addition salts thereof, wherein A is

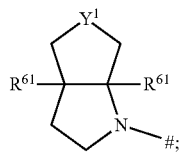

wherein $Y^1$ is O or $NR^{61}$;

each $R^{61}$ is independently H or methyl, preferably H; and # is the attachment point to the remainder of the molecule;

$X^1, X^2, X^3$ and $X^4$ are $CR^3$; where all radicals $R^3$ are H or three radicals $R^3$ are H and one radical $R^3$ is halogen or cyano;

$X^4, X^5$ and $X^6$ are CH;

$R^1$ is H;

$R^2$ is H; and $R^5$ is H.

Alternatively, particularly preferred compounds are compounds of formulae IA and IB the stereoisomers, prodrugs, tautomers and/or physiologically tolerated acid addition salts thereof, wherein A is

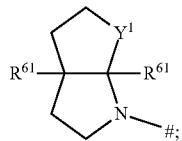

wherein $Y^1$ is O or $NR^{61}$;

each $R^{61}$ is independently H or methyl, preferably H; and # is the attachment point to the remainder of the molecule;

$X^1, X^2, X^3$ and $X^4$ are $CR^3$; where all radicals $R^3$ are H or three radicals $R^3$ are H and one radical $R^3$ is halogen or cyano;

$X^4, X^5$ and $X^6$ are CH;

$R^1$ is H;

$R^2$ is H; and $R^5$ is H.

Among compounds of formulae IA and IB, preference is given to compounds of formula IA.

Among compounds of formulae IA and IB, preference is given to compounds wherein A is a bicyclic or tricyclic ring and more preferably a bicyclic ring.

Suitable compounds IA and IB are those of formulae I.1 to I.30, the stereoisomers, prodrugs, tautomers and/or physiologically tolerated acid addition salts thereof, wherein A and $R^3$ have the above-defined general or preferred meanings. Particularly preferred meanings of A and $R^3$ in compounds of formula I and specifically in compounds of formulae I.1 to I.30 are as defined below.

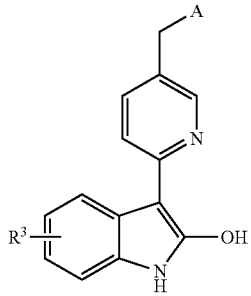

I.1

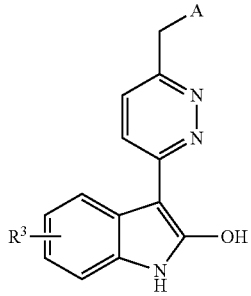

I.2

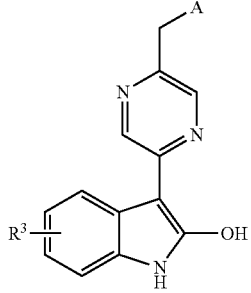

I.3

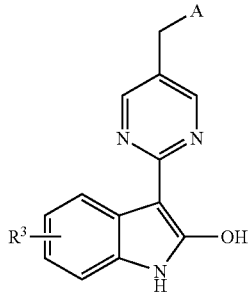

I.4

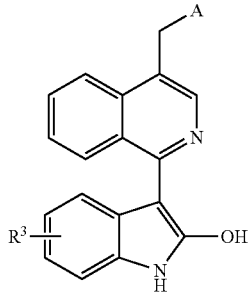

I.5

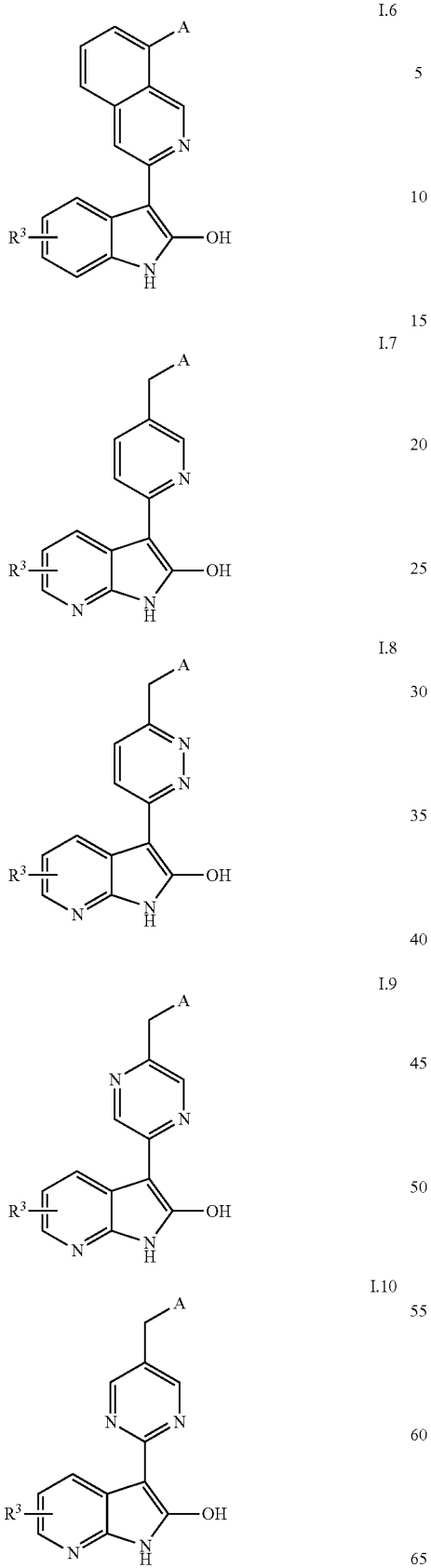
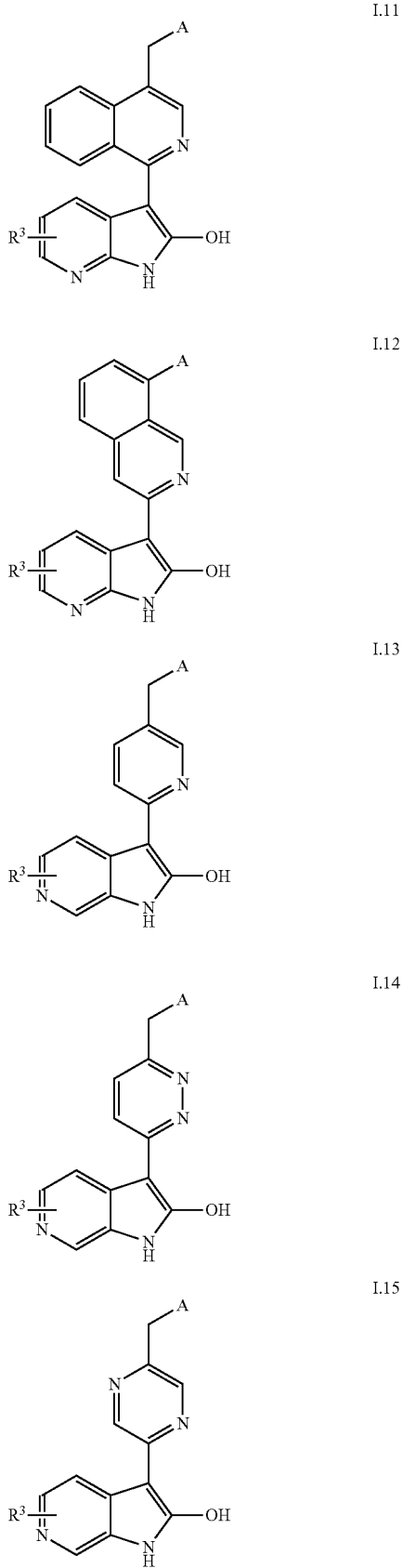

-continued
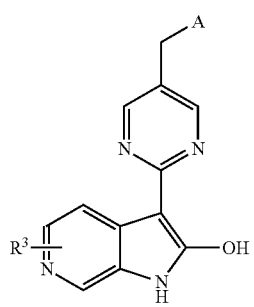
I-16
I-17
I-18
I-19
I-20
-continued
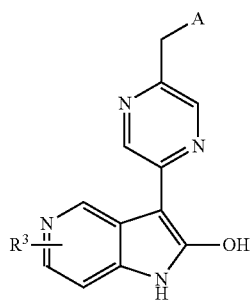
I-21
I-22
I-23
I-24
I-25

-continued
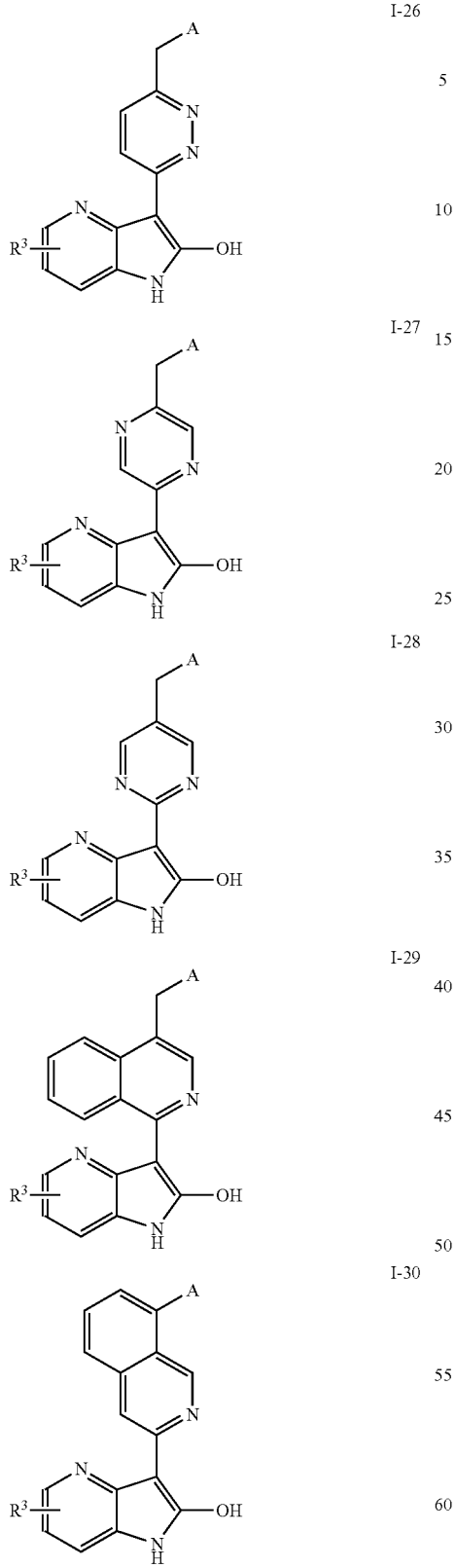
I-26
I-27
I-28
I-29
I-30
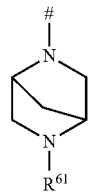 A.1
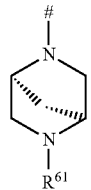 A.2
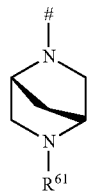 A.3
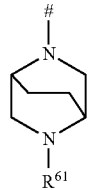 A.4
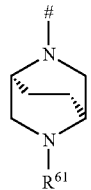 A.5
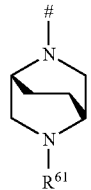 A.6
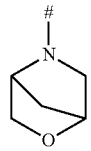 A.7
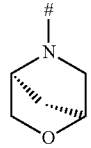 A.8
Preferred bicyclic groups A in compounds IA and IB and specifically in compounds of formulae I.1 to I.30 are selected from the radicals of the following formulae:

| | | | |
|---|---|---|---|
| 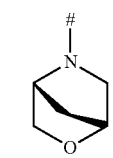 | A.9 |  | A.17 |
| 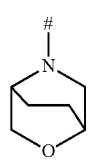 | A.10 |  | A.18 |
| 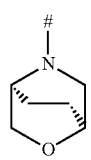 | A.11 | 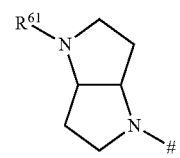 | A.19 |
| 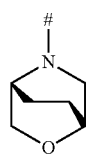 | A.12 | 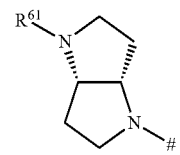 | A.20 |
| 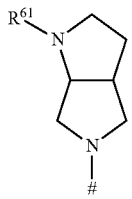 | A.13 | 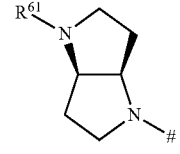 | A.21 |
| 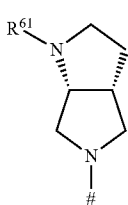 | A.14 | 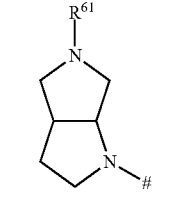 | A.22 |
| 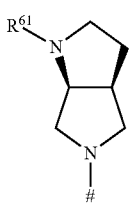 | A.15 | 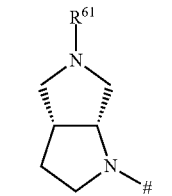 | A.23 |
|  | A.16 | 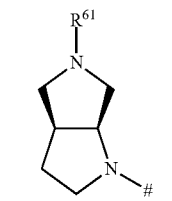 | A.24 |

| | |
|---|---|
| 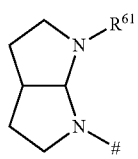 | A.25 |
| 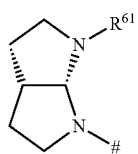 | A.26 |
| 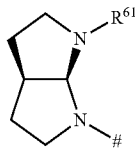 | A.27 |
| 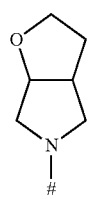 | A.28 |
| 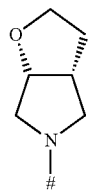 | A.29 |
| 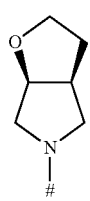 | A.30 |
| 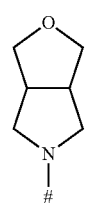 | A.31 |
| 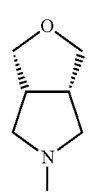 | A.32 |
| | |
|---|---|
|  | A.33 |
| 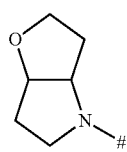 | A.34 |
| 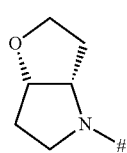 | A.35 |
| 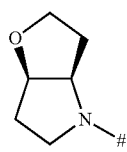 | A.36 |
| 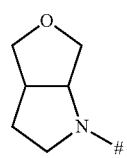 | A.37 |
| 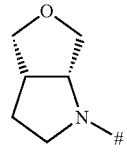 | A.38 |
| 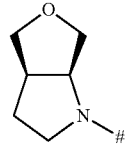 | A.39 |
| 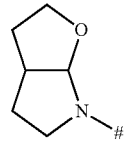 | A.40 |
| 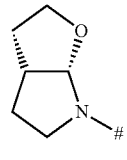 | A.41 |

A.42

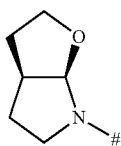

wherein $R^{61}$ is H or methyl and preferably H. "Normal" bonds in positions where they replace wedge or dotted bonds of neighbouring radicals symbolize all possible stereoisomers and mixtures of the respective stereoisomers.

Examples of preferred compounds which are represented by the formulae I.1 to I.30 are listed in following tables 1 to 14316 of U.S. Provisional Application No. 61/163,940, filed Mar. 27, 2009, the content of Tables 1 to 14316 are incorporated herein by reference. In the tables, the position of $R^3$ is characterized as follows:

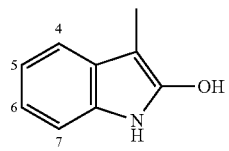

Table 1
Compounds of the formula I.1 in which $R^3$ is H, A is a group of formula A.1 and $R^{61}$ is selected from H, methyl, ethyl, n-propyl, isopropyl, n-butyl, sec-butyl, isobutyl, tert-butyl, methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl Table 2
Compounds of the formula I.1 in which $R^3$ is 4-Cl, A is a group of formula A.1 and $R^{61}$ has one of the meanings given in table 1

Table 3
Compounds of the formula I.1 in which $R^3$ is 5-Cl, A is a group of formula A.1 and $R^{61}$ has one of the meanings given in table 1

Table 4
Compounds of the formula I.1 in which $R^3$ is 6-Cl, A is a group of formula A.1 and $R^{61}$ has one of the meanings given in table 1

Table 5
Compounds of the formula I.1 in which $R^3$ is 7-Cl, A is a group of formula A.1 and $R^{61}$ has one of the meanings given in table 1

Table 6
Compounds of the formula I.1 in which $R^3$ is 4-Br, A is a group of formula A.1 and $R^{61}$ has one of the meanings given in table 1

Table 7
Compounds of the formula I.1 in which $R^3$ is 5-Br, A is a group of formula A.1 and $R^{61}$ has one of the meanings given in table 1

Table 8
Compounds of the formula I.1 in which $R^3$ is 6-Br, A is a group of formula A.1 and $R^{61}$ has one of the meanings given in table 1

Table 9
Compounds of the formula I.1 in which $R^3$ is 7-Br, A is a group of formula A.1 and $R^{61}$ has one of the meanings given in table 1

Table 10
Compounds of the formula I.1 in which $R^3$ is 4-CN, A is a group of formula A.1 and $R^{61}$ has one of the meanings given in table 1

Table 11
Compounds of the formula I.1 in which $R^3$ is 5-CN, A is a group of formula A.1 and $R^{61}$ has one of the meanings given in table 1

Table 12
Compounds of the formula I.1 in which $R^3$ is 6-CN A is a group of formula A.1 and $R^{61}$ has one of the meanings given in table 1

Table 13
Compounds of the formula I.1 in which $R^3$ is 7-CN, A is a group of formula A.1 and $R^{61}$ has one of the meanings given in table 1

Tables 14 to 26
Compounds of the formula I.1 in which A is a group of formula A.2, $R^{61}$ has one of the meanings given in table 1 and $R^3$ has one of the meanings given in tables 1 to 13

Tables 27 to 39
Compounds of the formula I.1 in which A is a group of formula A.3, $R^{61}$ has one of the meanings given in table I and $R^3$ has one of the meanings given in tables 1 to 13

Tables 40 to 52
Compounds of the formula I.1 in which A is a group of formula A.4, $R^{61}$ has one of the meanings given in table 1 and $R^3$ has one of the meanings given in tables 1 to 13

Tables 53 to 65
Compounds of the formula I.1 in which A is a group of formula A.5, $R^{61}$ has one of the meanings given in table 1 and $R^3$ has one of the meanings given in tables 1 to 13

Tables 66 to 78
Compounds of the formula I.1 in which A is a group of formula A.6, $R^{61}$ has one of the meanings given in table 1 and $R^3$ has one of the meanings given in tables 1 to 13

Tables 79 to 91
Compounds of the formula I.1 in which A is a group of formula A.7, $R^{61}$ has one of the meanings given in table 1 and $R^3$ has one of the meanings given in tables 1 to 13

Tables 92 to 104
Compounds of the formula I.1 in which A is a group of formula A.8, $R^{61}$ has one of the meanings given in table 1 and $R^3$ has one of the meanings given in tables 1 to 13

Tables 105 to 117
Compounds of the formula I.1 in which A is a group of formula A.9, $R^{61}$ has one of the meanings given in table 1 and $R^3$ has one of the meanings given in tables 1 to 13

Tables 118 to 130
Compounds of the formula I.1 in which A is a group of formula A.10, $R^{61}$ has one of the meanings given in table 1 and $R^3$ has one of the meanings given in tables 1 to 13

Tables 131 to 143
Compounds of the formula I.1 in which A is a group of formula A.11, $R^{61}$ has one of the meanings given in table 1 and $R^3$ has one of the meanings given in tables 1 to 13

Tables 144 to 156
Compounds of the formula I.1 in which A is a group of formula A.12, $R^{61}$ has one of the meanings given in table 1 and $R^3$ has one of the meanings given in tables 1 to 13

Tables 157 to 169
Compounds of the formula I.1 in which A is a group of formula A.13, $R^{61}$ has one of the meanings given in table 1 and $R^3$ has one of the meanings given in tables 1 to 13

Tables 170 to 182
Compounds of the formula I.1 in which A is a group of formula A.14, $R^{61}$ has one of the meanings given in table 1 and $R^3$ has one of the meanings given in tables 1 to 13

Tables 183 to 195
Compounds of the formula I.1 in which A is a group of formula A.15, $R^{61}$ has one of the meanings given in table 1 and $R^3$ has one of the meanings given in tables 1 to 13

Tables 196 to 208
Compounds of the formula I.1 in which A is a group of formula A.16, $R^{61}$ has one of the meanings given in table 1 and $R^3$ has one of the meanings given in tables 1 to 13

Tables 209 to 221
Compounds of the formula I.1 in which A is a group of formula A.17, $R^{61}$ has one of the meanings given in table 1 and $R^3$ has one of the meanings given in tables 1 to 13

Tables 222 to 234
Compounds of the formula I.1 in which A is a group of formula A.18, $R^{61}$ has one of the meanings given in table 1 and $R^3$ has one of the meanings given in tables 1 to 13

Tables 235 to 247
Compounds of the formula I.1 in which A is a group of formula A.19, $R^{61}$ has one of the meanings given in table 1 and $R^3$ has one of the meanings given in tables 1 to 13

Tables 248 to 260
Compounds of the formula I.1 in which A is a group of formula A.20, $R^{61}$ has one of the meanings given in table 1 and $R^3$ has one of the meanings given in tables 1 to 13

Tables 261 to 273
Compounds of the formula I.1 in which A is a group of formula A.21, $R^{61}$ has one of the meanings given in table 1 and $R^3$ has one of the meanings given in tables 1 to 13

Tables 274 to 286
Compounds of the formula I.1 in which A is a group of formula A.22, $R^{61}$ has one of the meanings given in table 1 and $R^3$ has one of the meanings given in tables 1 to 13

Tables 287 to 299
Compounds of the formula I.1 in which A is a group of formula A.23, $R^{61}$ has one of the meanings given in table 1 and $R^3$ has one of the meanings given in tables 1 to 13

Tables 300 to 312
Compounds of the formula I.1 in which A is a group of formula A.24, $R^{61}$ has one of the meanings given in table 1 and $R^3$ has one of the meanings given in tables 1 to 13

Tables 313 to 325
Compounds of the formula I.1 in which A is a group of formula A.25, $R^{61}$ has one of the meanings given in table 1 and $R^3$ has one of the meanings given in tables 1 to 13

Tables 326 to 338
Compounds of the formula I.1 in which A is a group of formula A.26, $R^{61}$ has one of the meanings given in table I and $R^3$ has one of the meanings given in tables 1 to 13

Tables 339 to 351
Compounds of the formula I.1 in which A is a group of formula A.27, $R^{61}$ has one of the meanings given in table 1 and $R^3$ has one of the meanings given in tables 1 to 13

Tables 352 to 364
Compounds of the formula I.1 in which A is a group of formula A.28 and $R^3$ has one of the meanings given in tables 1 to 13

Tables 365 to 377
Compounds of the formula I.1 in which A is a group of formula A.29 and $R^3$ has one of the meanings given in tables 1 to 13

Tables 378 to 390
Compounds of the formula I.1 in which A is a group of formula A.30 and $R^3$ has one of the meanings given in tables 1 to 13

Tables 391 to 403
Compounds of the formula I.1 in which A is a group of formula A.31 and $R^3$ has one of the meanings given in tables 1 to 13

Tables 404 to 416
Compounds of the formula I.1 in which A is a group of formula A.32 and $R^3$ has one of the meanings given in tables 1 to 13

Tables 417 to 429
Compounds of the formula I.1 in which A is a group of formula A.33 and $R^3$ has one of the meanings given in tables 1 to 13

Tables 430 to 442
Compounds of the formula I.1 in which A is a group of formula A.34 and $R^3$ has one of the meanings given in tables 1 to 13

Tables 443 to 455
Compounds of the formula I.1 in which A is a group of formula A.35 and $R^3$ has one of the meanings given in tables 1 to 13

Tables 456 to 468
Compounds of the formula I.1 in which A is a group of formula A.36 and $R^3$ has one of the meanings given in tables 1 to 13

Tables 469 to 481
Compounds of the formula I.1 in which A is a group of formula A.37 and $R^3$ has one of the meanings given in tables 1 to 13

Tables 482 to 494
Compounds of the formula I.1 in which A is a group of formula A.38 and $R^3$ has one of the meanings given in tables 1 to 13

Tables 495 to 507
Compounds of the formula I.1 in which A is a group of formula A.39 and $R^3$ has one of the meanings given in tables 1 to 13

Tables 508 to 520
Compounds of the formula I.1 in which A is a group of formula A.40 and $R^3$ has one of the meanings given in tables 1 to 13

Tables 521 to 533
Compounds of the formula I.1 in which A is a group of formula A.41 and $R^3$ has one of the meanings given in tables 1 to 13

Tables 534 to 546
Compounds of the formula I.1 in which A is a group of formula A.42 and $R^3$ has one of the meanings given in tables 1 to 13

Tables 547 to 1092
Compounds of the formula I.2 in which the combination of A, $R^{61}$ and $R^3$ is as defined in tables 1 to 546

Tables 1093 to 1638
Compounds of the formula I.3 in which the combination of A, $R^{61}$ and $R^3$ is as defined in tables 1 to 546

Tables 1639 to 2184
Compounds of the formula I.4 in which the combination of A, $R^{61}$ and $R^3$ is as defined in tables 1 to 546

Tables 2185 to 2730
Compounds of the formula I.5 in which the combination of A, $R^{61}$ and $R^3$ is as defined in tables 1 to 546

Tables 2731 to 3276
Compounds of the formula I.6 in which the combination of A, $R^{61}$ and $R^3$ is as defined in tables 1 to 546

Table 3277
Compounds of the formula I.7 in which $R^3$ is H and A is pyrrolidin-1-yl
Table 3278
Compounds of the formula I.7 in which $R^3$ is 4-Cl and A is pyrrolidin-1-yl
Table 3279
Compounds of the formula I.7 in which $R^3$ is 5-Cl and A is pyrrolidin-1-yl
Table 3280
Compounds of the formula I.7 in which $R^3$ is 6-Cl and A is pyrrolidin-1-yl
Table 3281
Compounds of the formula I.7 in which $R^3$ is 4-Br and A is pyrrolidin-1-yl
Table 3282
Compounds of the formula I.7 in which $R^3$ is 5-Br and A is pyrrolidin-1-yl
Table 3283
Compounds of the formula I.7 in which $R^3$ is 6-Br and A is pyrrolidin-1-yl
Table 3284
Compounds of the formula I.7 in which $R^3$ is 4-CN and A is pyrrolidin-1-yl
Table 3285
Compounds of the formula I.7 in which $R^3$ is 5-CN and A is pyrrolidin-1-yl
Table 3286
Compounds of the formula I.7 in which $R^3$ is 6-CN and A is pyrrolidin-1-yl
Tables 3287 to 3296
Compounds of the formula I.7 in which A is piperidin-1-yl and $R^3$ has one of the meanings given in tables 3277 to 3286
Tables 3297 to 3306
Compounds of the formula I.7 in which A is piperazin-1-yl and $R^3$ has one of the meanings given in tables 3277 to 3286
Tables 3307 to 3316
Compounds of the formula I.7 in which A is morpholin-4-yl and $R^{61}$ has one of the meanings given in tables 3277 to 3286
Tables 3317 to 3326
Compounds of the formula I.7 in which A is a group of formula A.1, $R^{61}$ has one of the meanings given in table 1 and $R^3$ has one of the meanings given in tables 3277 to 3286
Tables 3327 to 3336
Compounds of the formula I.7 in which A is a group of formula A.2, $R^{61}$ has one of the meanings given in table 1 and $R^3$ has one of the meanings given in tables 3277 to 3286
Tables 3337 to 3346
Compounds of the formula I.7 in which A is a group of formula A.3, $R^{61}$ has one of the meanings given in table 1 and $R^3$ has one of the meanings given in tables 3277 to 3286
Tables 3347 to 3356
Compounds of the formula I.7 in which A is a group of formula A.4, $R^{61}$ has one of the meanings given in table 1 and $R^3$ has one of the meanings given in tables 3277 to 3286
Tables 3357 to 3366
Compounds of the formula I.7 in which A is a group of formula A.5, $R^{61}$ has one of the meanings given in table 1 and $R^3$ has one of the meanings given in tables 3277 to 3286
Tables 3367 to 3376
Compounds of the formula I.7 in which A is a group of formula A.6, $R^{61}$ has one of the meanings given in table 1 and $R^3$ has one of the meanings given in tables 3277 to 3286
Tables 3377 to 3386
Compounds of the formula I.7 in which A is a group of formula A.7, $R^{61}$ has one of the meanings given in table 1 and $R^3$ has one of the meanings given in tables 3277 to 3286
Tables 3387 to 3396
Compounds of the formula I.7 in which A is a group of formula A.8, $R^{61}$ has one of the meanings given in table 1 and $R^3$ has one of the meanings given in tables 3277 to 3286
Tables 3397 to 3406
Compounds of the formula I.7 in which A is a group of formula A.9, $R^{61}$ has one of the meanings given in table 1 and $R^3$ has one of the meanings given in tables 3277 to 3286
Tables 3407 to 3416
Compounds of the formula I.7 in which A is a group of formula A.10, $R^{61}$ has one of the meanings given in table 1 and $R^3$ has one of the meanings given in tables 3277 to 3286
Tables 3417 to 3426
Compounds of the formula I.7 in which A is a group of formula A.11, $R^{61}$ has one of the meanings given in table 1 and $R^3$ has one of the meanings given in tables 3277 to 3286
Tables 3427 to 3436
Compounds of the formula I.7 in which A is a group of formula A.12, $R^{61}$ has one of the meanings given in table 1 and $R^3$ has one of the meanings given in tables 3277 to 3286
Tables 3437 to 3446
Compounds of the formula I.7 in which A is a group of formula A.13, $R^{61}$ has one of the meanings given in table 1 and $R^3$ has one of the meanings given in tables 3277 to 3286
Tables 3447 to 3456
Compounds of the formula I.7 in which A is a group of formula A.14, $R^{61}$ has one of the meanings given in table 1 and $R^3$ has one of the meanings given in tables 3277 to 3286
Tables 3457 to 3466
Compounds of the formula I.7 in which A is a group of formula A.15, $R^{61}$ has one of the meanings given in table 1 and $R^3$ has one of the meanings given in tables 3277 to 3286
Tables 3467 to 3476
Compounds of the formula I.7 in which A is a group of formula A.16, $R^{61}$ has one of the meanings given in table 1 and $R^3$ has one of the meanings given in tables 3277 to 3286
Tables 3477 to 3486
Compounds of the formula I.7 in which A is a group of formula A.17, $R^{61}$ has one of the meanings given in table 1 and $R^3$ has one of the meanings given in tables 3277 to 3286
Tables 3487 to 3496
Compounds of the formula I.7 in which A is a group of formula A.18, $R^{61}$ has one of the meanings given in table 1 and $R^3$ has one of the meanings given in tables 3277 to 3286
Tables 3497 to 3506
Compounds of the formula I.7 in which A is a group of formula A.19, $R^{61}$ has one of the meanings given in table 1 and $R^3$ has one of the meanings given in tables 3277 to 3286
Tables 3507 to 3516
Compounds of the formula I.7 in which A is a group of formula A.20, $R^{61}$ has one of the meanings given in table 1 and $R^3$ has one of the meanings given in tables 3277 to 3286
Tables 3517 to 3526
Compounds of the formula I.7 in which A is a group of formula A.21, $R^{61}$ has one of the meanings given in table 1 and $R^3$ has one of the meanings given in tables 3277 to 3286
Tables 3527 to 3536
Compounds of the formula I.7 in which A is a group of formula A.22, $R^{61}$ has one of the meanings given in table 1 and $R^3$ has one of the meanings given in tables 3277 to 3286

Tables 3537 to 3546

Compounds of the formula I.7 in which A is a group of formula A.23, $R^{61}$ has one of the meanings given in table 1 and $R^3$ has one of the meanings given in tables 3277 to 3286

Tables 3547 to 3556

Compounds of the formula I.7 in which A is a group of formula A.24, $R^{61}$ has one of the meanings given in table 1 and $R^3$ has one of the meanings given in tables 3277 to 3286

Tables 3557 to 3566

Compounds of the formula I.7 in which A is a group of formula A.25, $R^{61}$ has one of the meanings given in table 1 and $R^3$ has one of the meanings given in tables 3277 to 3286

Tables 3567 to 3576

Compounds of the formula I.7 in which A is a group of formula A.26, $R^{61}$ has one of the meanings given in table 1 and $R^3$ has one of the meanings given in tables 3277 to 3286

Tables 3577 to 3586

Compounds of the formula I.7 in which A is a group of formula A.27, $R^{61}$ has one of the meanings given in table 1 and $R^3$ has one of the meanings given in tables 3277 to 3286

Tables 3587 to 3596

Compounds of the formula I.7 in which A is a group of formula A.28 and $R^3$ has one of the meanings given in tables 3277 to 3286

Tables 3597 to 3606

Compounds of the formula I.7 in which A is a group of formula A.29 and $R^3$ has one of the meanings given in tables 3277 to 3286

Tables 3607 to 3616

Compounds of the formula I.7 in which A is a group of formula A.30 and $R^3$ has one of the meanings given in tables 3277 to 3286

Tables 3617 to 3626

Compounds of the formula I.7 in which A is a group of formula A.31 and $R^3$ has one of the meanings given in tables 3277 to 3286

Tables 3627 to 3636

Compounds of the formula I.7 in which A is a group of formula A.32 and $R^3$ has one of the meanings given in tables 3277 to 3286

Tables 3637 to 3646

Compounds of the formula I.7 in which A is a group of formula A.33 and $R^3$ has one of the meanings given in tables 3277 to 3286

Tables 3647 to 3656

Compounds of the formula I.7 in which A is a group of formula A.34 and $R^3$ has one of the meanings given in tables 3277 to 3286

Tables 3657 to 3666

Compounds of the formula I.7 in which A is a group of formula A.35 and $R^3$ has one of the meanings given in tables 3277 to 3286

Tables 3667 to 3676

Compounds of the formula I.7 in which A is a group of formula A.36 and $R^3$ has one of the meanings given in tables 3277 to 3286

Tables 3677 to 3686

Compounds of the formula I.7 in which A is a group of formula A.37 and $R^3$ has one of the meanings given in tables 3277 to 3286

Tables 3687 to 3696

Compounds of the formula I.7 in which A is a group of formula A.38 and $R^3$ has one of the meanings given in tables 3277 to 3286

Tables 3697 to 3706

Compounds of the formula I.7 in which A is a group of formula A.39 and $R^3$ has one of the meanings given in tables 3277 to 3286

Tables 3707 to 3716

Compounds of the formula I.7 in which A is a group of formula A.40 and $R^3$ has one of the meanings given in tables 3277 to 3286

Tables 3717 to 3726

Compounds of the formula I.7 in which A is a group of formula A.41 and $R^6$ has one of the meanings given in tables 3277 to 3286

Tables 3727 to 3736

Compounds of the formula I.7 in which A is a group of formula A.42 and $R^3$ has one of the meanings given in tables 3277 to 3286

Tables 3777 to 4196

Compounds of the formula I.8 in which the combination of A, $R^{61}$ and $R^3$ is as defined in tables 3277 to 3776

Tables 4197 to 4656

Compounds of the formula I.9 in which the combination of A, $R^{61}$ and $R^3$ is as defined in tables 3277 to 3776

Tables 4657 to 5116

Compounds of the formula I.10 in which the combination of A, $R^{61}$ and $R^3$ is as defined in tables 3277 to 3776

Tables 5117 to 5576

Compounds of the formula I.11 in which the combination of A, $R^{61}$ and $R^3$ is as defined in tables 3277 to 3776

Tables 5577 to 6036

Compounds of the formula I.12 in which the combination of A, $R^{61}$ and $R^3$ is as defined in tables 3277 to 3776

Tables 6037 to 6082

Compounds of the formula I.13 in which A has one of the meanings given in tables 3277 to 3736, $R^{61}$ has one of the meanings given in table 1 and $R^3$ is H Tables 6083 to 6128

Compounds of the formula I.13 in which A has one of the meanings given in tables 3277 to 3736, $R^{61}$ has one of the meanings given in table 1 and $R^3$ is 4-Cl Tables 6129 to 6174

Compounds of the formula I.13 in which A has one of the meanings given in tables 3277 to 3736, $R^{61}$ has one of the meanings given in table 1 and $R^3$ is 5-Cl Tables 6175 to 6220

Compounds of the formula I.13 in which A has one of the meanings given in tables 3277 to 3736, $R^{61}$ has one of the meanings given in table 1 and $R^3$ is 7-Cl Tables 6221 to 6266

Compounds of the formula I.13 in which A has one of the meanings given in tables 3277 to 3736, $R^{61}$ has one of the meanings given in table 1 and $R^3$ is 4-Br Tables 6267 to 6312

Compounds of the formula I.13 in which A has one of the meanings given in tables 3277 to 3736, $R^{61}$ has one of the meanings given in table 1 and $R^3$ is 5-Br Tables 6313 to 6358

Compounds of the formula I.13 in which A has one of the meanings given in tables 3277 to 3736, $R^{61}$ has one of the meanings given in table 1 and $R^3$ is 7-Br Tables 6359 to 6404

Compounds of the formula I.13 in which A has one of the meanings given in tables 3277 to 3736, $R^{61}$ has one of the meanings given in table 1 and $R^3$ is 4-CN Tables 6405 to 6450

Compounds of the formula I.13 in which A has one of the meanings given in tables 3277 to 3736, $R^{61}$ has one of the meanings given in table 1 and $R^3$ is 5-CN Tables 6451 to 6496
Compounds of the formula I.13 in which A has one of the meanings given in tables 3277 to 3736, $R^{61}$ has one of the meanings given in table 1 and $R^3$ is 7-CN
Tables 6497 to 6956
Compounds of the formula I.14 in which the combination of A, $R^{61}$ and $R^3$ is as defined in tables 6037 to 6496
Tables 6957 to 7416
Compounds of the formula I.15 in which the combination of A, $R^{61}$ and $R^3$ is as defined in tables 6037 to 6496
Tables 7417 to 7876
Compounds of the formula I.16 in which the combination of A, $R^{61}$ and $R^3$ is as defined in tables 6037 to 6496
Tables 7877 to 8336
Compounds of the formula I.17 in which the combination of A, $R^{61}$ and $R^3$ is as defined in tables 6037 to 6496
Tables 8337 to 8796
Compounds of the formula I.18 in which the combination of A, $R^{61}$ and $R^3$ is as defined in tables 6037 to 6496
Tables 8797 to 8842
Compounds of the formula I.19 in which A has one of the meanings given in tables 3277 to 3736, $R^{61}$ has one of the meanings given in table 1 and $R^3$ is H
Tables 8843 to 8888
Compounds of the formula I.19 in which A has one of the meanings given in tables 3277 to 3736, $R^{61}$ has one of the meanings given in table 1 and $R^3$ is 4-Cl
Tables 8889 to 8934
Compounds of the formula I.19 in which A has one of the meanings given in tables 3277 to 3736, $R^{61}$ has one of the meanings given in table 1 and $R^3$ is 6-Cl
Tables 8935 to 8980
Compounds of the formula I.19 in which A has one of the meanings given in tables 3277 to 3736, $R^{61}$ has one of the meanings given in table 1 and $R^3$ is 7-Cl
Tables 8981 to 9026
Compounds of the formula I.19 in which A has one of the meanings given in tables 3277 to 3736, $R^{61}$ has one of the meanings given in table 1 and $R^3$ is 4-Br
Tables 9027 to 9072
Compounds of the formula I.19 in which A has one of the meanings given in tables 3277 to 3736, $R^{61}$ has one of the meanings given in table 1 and $R^3$ is 6-Br
Tables 9073 to 9118
Compounds of the formula I.19 in which A has one of the meanings given in tables 3277 to 3736, $R^{61}$ has one of the meanings given in table 1 and $R^3$ is 7-Br
Tables 9119 to 9164
Compounds of the formula I.19 in which A has one of the meanings given in tables 3277 to 3736, $R^{61}$ has one of the meanings given in table 1 and $R^3$ is 4-CN
Tables 9165 to 9210
Compounds of the formula I.19 in which A has one of the meanings given in tables 3277 to 3736, $R^{61}$ has one of the meanings given in table 1 and $R^3$ is 6-CN
Tables 9211 to 9256
Compounds of the formula I.19 in which A has one of the meanings given in tables 3277 to 3736, $R^{61}$ has one of the meanings given in table 1 and $R^3$ is 7-CN
Tables 9257 to 9716
Compounds of the formula I.20 in which the combination of A, $R^{61}$ and $R^3$ is as defined in tables 8797 to 9256
Tables 9717 to 10176
Compounds of the formula I.21 in which the combination of A, $R^{61}$ and $R^3$ is as defined in tables 8797 to 9256
Tables 10177 to 10636
Compounds of the formula I.22 in which the combination of A, $R^{61}$ and $R^3$ is as defined in tables 8797 to 9256
Tables 10637 to 11096
Compounds of the formula I.23 in which the combination of A, $R^{61}$ and $R^3$ is as defined in tables 8797 to 9256
Tables 11097 to 11556
Compounds of the formula I.24 in which the combination of A, $R^{61}$ and $R^3$ is as defined in tables 8797 to 9256
Tables 11557 to 11602
Compounds of the formula I.25 in which A has one of the meanings given in tables 3277 to 3736, $R^{61}$ has one of the meanings given in table 1 and $R^3$ is H
Tables 11603 to 11648
Compounds of the formula I.25 in which A has one of the meanings given in tables 3277 to 3736, $R^{61}$ has one of the meanings given in table 1 and $R^3$ is 5-Cl
Tables 11649 to 11694
Compounds of the formula I.25 in which A has one of the meanings given in tables 3277 to 3736, $R^{61}$ has one of the meanings given in table 1 and $R^3$ is 6-Cl
Tables 11695 to 11740
Compounds of the formula I.25 in which A has one of the meanings given in tables 3277 to 3736, $R^{61}$ has one of the meanings given in table 1 and $R^3$ is 7-Cl
Tables 11741 to 11786
Compounds of the formula I.25 in which A has one of the meanings given in tables 3277 to 3736, $R^{61}$ has one of the meanings given in table 1 and $R^3$ is 5-Br
Tables 11787 to 11832
Compounds of the formula I.25 in which A has one of the meanings given in tables 3277 to 3736, $R^{61}$ has one of the meanings given in table 1 and $R^3$ is 6-Br
Tables 11833 to 11878
Compounds of the formula I.25 in which A has one of the meanings given in tables 3277 to 3736, $R^{61}$ has one of the meanings given in table 1 and $R^3$ is 7-Br
Tables 11879 to 11924
Compounds of the formula I.25 in which A has one of the meanings given in tables 3277 to 3736, $R^{61}$ has one of the meanings given in table 1 and $R^3$ is 5-CN
Tables 11925 to 11970
Compounds of the formula I.25 in which A has one of the meanings given in tables 3277 to 3736, $R^{61}$ has one of the meanings given in table 1 and $R^3$ is 6-CN
Tables 11971 to 12016
Compounds of the formula I.25 in which A has one of the meanings given in tables 3277 to 3736, $R^{61}$ has one of the meanings given in table 1 and $R^3$ is 7-CN
Tables 12017 to 12476
Compounds of the formula I.26 in which the combination of A, $R^{61}$ and $R^3$ is as defined in tables 11557 to 12016
Tables 12477 to 12936
Compounds of the formula I.27 in which the combination of A, $R^{61}$ and $R^3$ is as defined in tables 11557 to 12016
Tables 12937 to 13396
Compounds of the formula I.28 in which the combination of A, $R^{61}$ and $R^3$ is as defined in tables 11557 to 12016
Tables 13397 to 13856
Compounds of the formula I.29 in which the combination of A, $R^{61}$ and $R^3$ is as defined in tables 11557 to 12016
Tables 13857 to 14316
Compounds of the formula I.30 in which the combination of A, $R^{61}$ and $R^3$ is as defined in tables 11557 to 12016

Among the above compounds of formulae I.1 to I.30 preference is given to compounds of formulae I.1, I.7, I.13, I.19 and I.25. Particular preference is given to compounds of formula I.1.

The compounds of the present invention can be prepared by analogy to routine techniques a skilled person is familiar with. In particular, the compounds of the formula IA and IB can be prepared according to the following schemes, wherein the variables, if not stated otherwise, are as defined above. In the below schemes, compounds of formula IA are expressed as target molecules. However, the same reactions apply to the syntheses of compounds IB. A' in the below schemes has one of the definitions given above for A. If A however contains more than one nitrogen ring atom, then A', where appropriate, is a group A wherein this/these further nitrogen ring atom(s) carries/carry a protective group, such as boc or ethylcarbonyloxy.

Scheme 1:

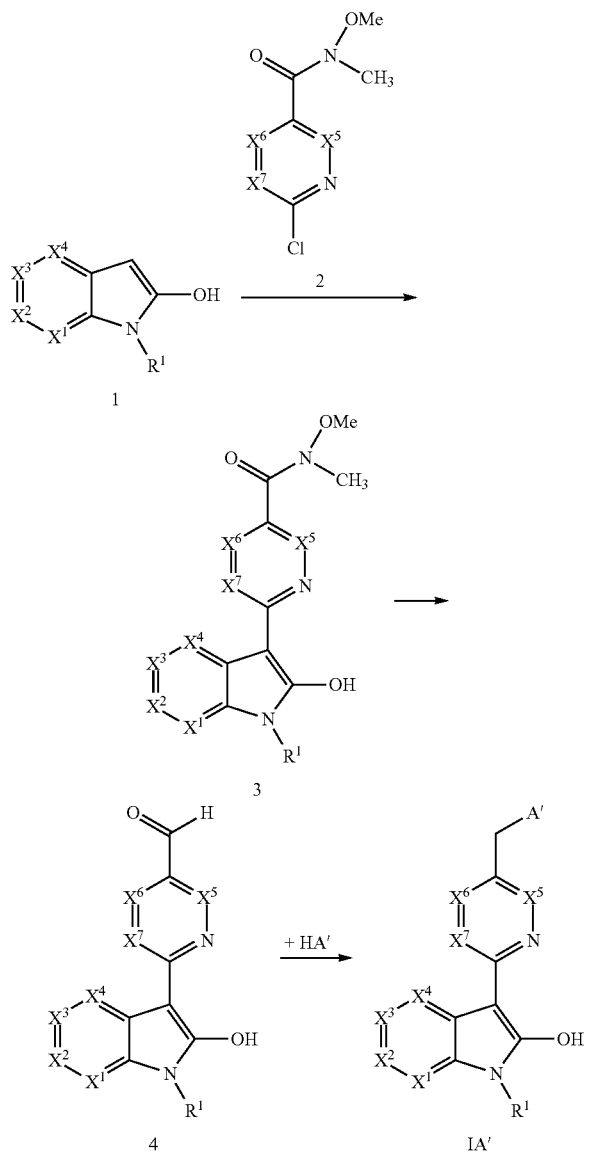

Alternatively, for preparing compounds IA/IB wherein $R^5$ is H, the 2-hydroxyindole 1 can be first deprotonated at the 3-position and then be reacted with the Weinreb amide 2. Deprotonation can be carried out with a suitable base, such as sodium hydride, in a suitable solvent. Suitable solvents are polar aprotic, e.g. $C_3$-$C_4$-ketones, such as acetone and ethylmethylketone, cyclic ethers, such as tetrahydrofuran and dioxane, dimethylsulfoxide and, in particular, amides, such as dimethylformamide (DMF) and dimethylacetamide. Both the deprotonation reaction as well as the reaction with the Weinreb amide generally takes place at elevated temperature, e.g. at from 40 to 150° C. Reduction of the resulting amide 3, for example with LiAlH$_4$, yields the aldehyde 4, which is then subjected to a reductive amination with the compound H-A'. Reduction can for example be accomplished by reacting the direct reaction product of 4 and H-A' with a suitable reduction agent, for example a borohydride, such as triacetoxyborohydride. The Weinreb amide 2 can be prepared by reacting the carbonyl chloride of compound 2 (e.g. 2-chloronicotinoyl chloride) with N-methoxy-N-methylamine.

Scheme 2:

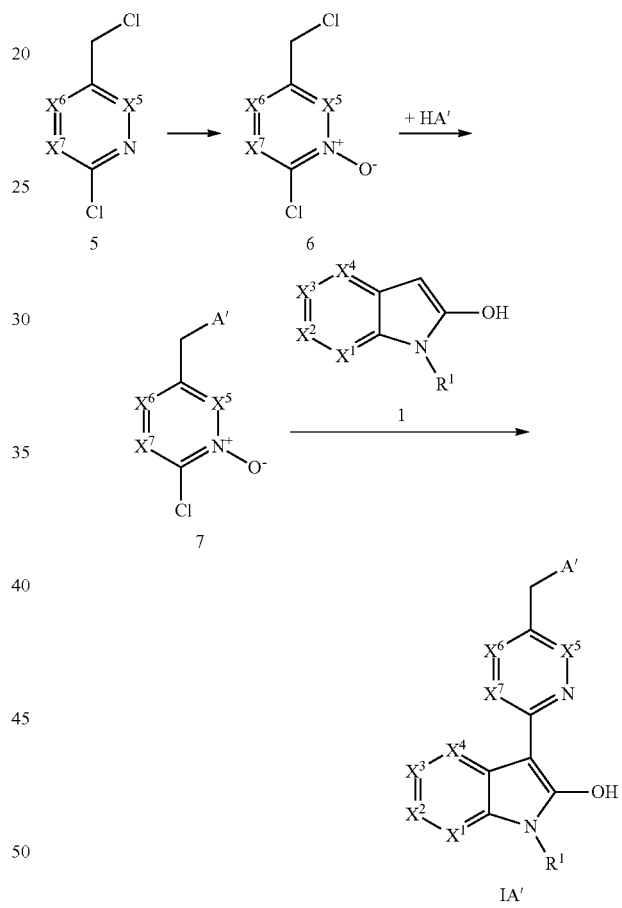

Alternatively, for preparing compounds IA/IB wherein $R^5$ is H, the 2-hydroxyindole 1 can be reacted with the chloro compound 7 in analogy to the reaction of 1 and 2 described above in scheme 1. This reaction results in the N-oxide of the compound IA', which, if desired, can be reduced to give a compound IA'. A suitable reduction agent is phosphorus trichloride. Compound 7 can be prepared by reacting the dichloro compound 6 with H-A', suitably in the presence of a base. Suitable bases are both inorganic bases, such as sodium or potassium hydroxide or sodium or potassium carbonate, as well as organic amines, such as triethylamine or Hünig's base, alkanolamines, such as triethanolamine, and basic heterocycles, such as pyridine, lutidine, DBU, DBN or DABCO. Compound 6 can be prepared by N-oxidizing compound 5, e.g. with meta-chloroperbenzoic acid.

Scheme 3:
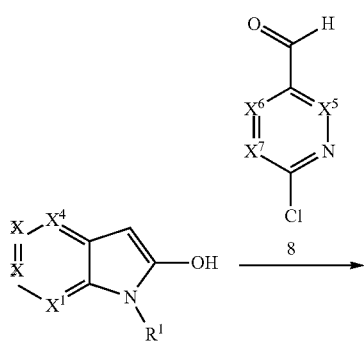
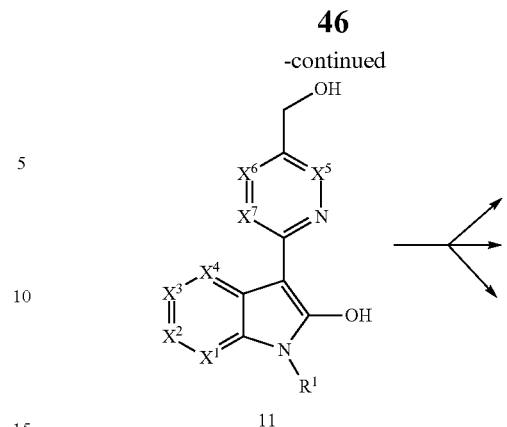
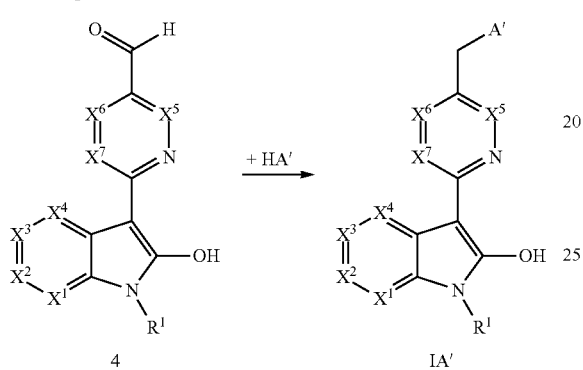
Alternatively, for preparing compounds IA/IB wherein $R^5$ is H, the 2-hydroxyindole 1 can be directly reacted with the aldehyde 8 in analogy to the reaction of 1 and 2 described above in scheme 1 and in analogy to the reaction described in J. Am. Chem. Soc. 2008, 130, 9613-9620. The reaction of the resulting compound 4 to IA' can be carried out as described above in scheme 1.
Scheme 4
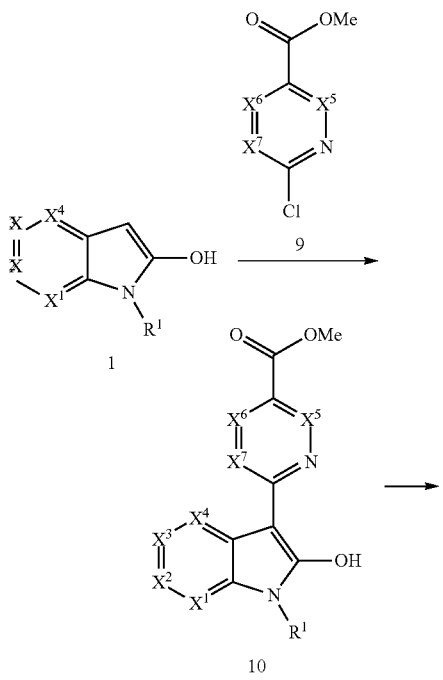
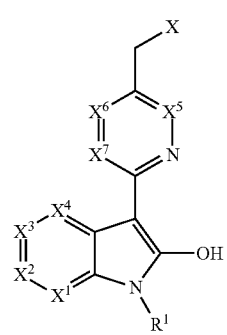
12
X = Cl, Br
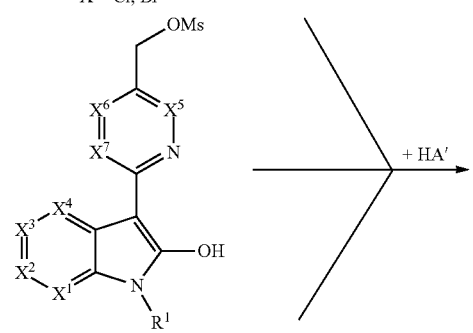
13
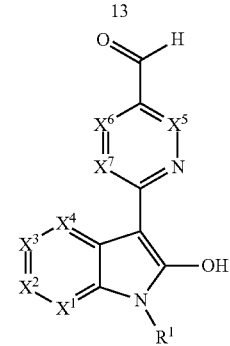
4

-continued

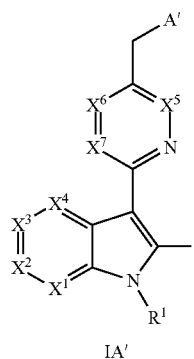

IA'

Alternatively, for preparing compounds IA/IB wherein $R^5$ is H, compounds 12 or 13 can be reacted with H-A' in analogy to the reaction of 6 and H-A' described in scheme 2. The reaction of compound 4 with H-A' can be carried out as described above in scheme 1. Compound 12 can be prepared from the benzylic alcohol 11 by reaction with HCl, thionyl chloride, phorphorus trichloride, phosphorus pentachloride or the like. Mesylation of the alcohol 11 yields 13. Oxidation of 11 with a suitable oxidizing agent, for example, chromium (IV) oxide, chromic acid, tert-butylchromate, pyridinium dichromate, $MnO_2$, potassium ferrate, etc., yields aldehyde 4. The benzylic alcohol 11 can be prepared by reacting 1 with ester 9 and reducing the ester group of the resulting compound 10 with a suitable reduction agent, such as $LiAlH_4$, $NaBH_4$, $LiBH_4$ and the like.

Scheme 5

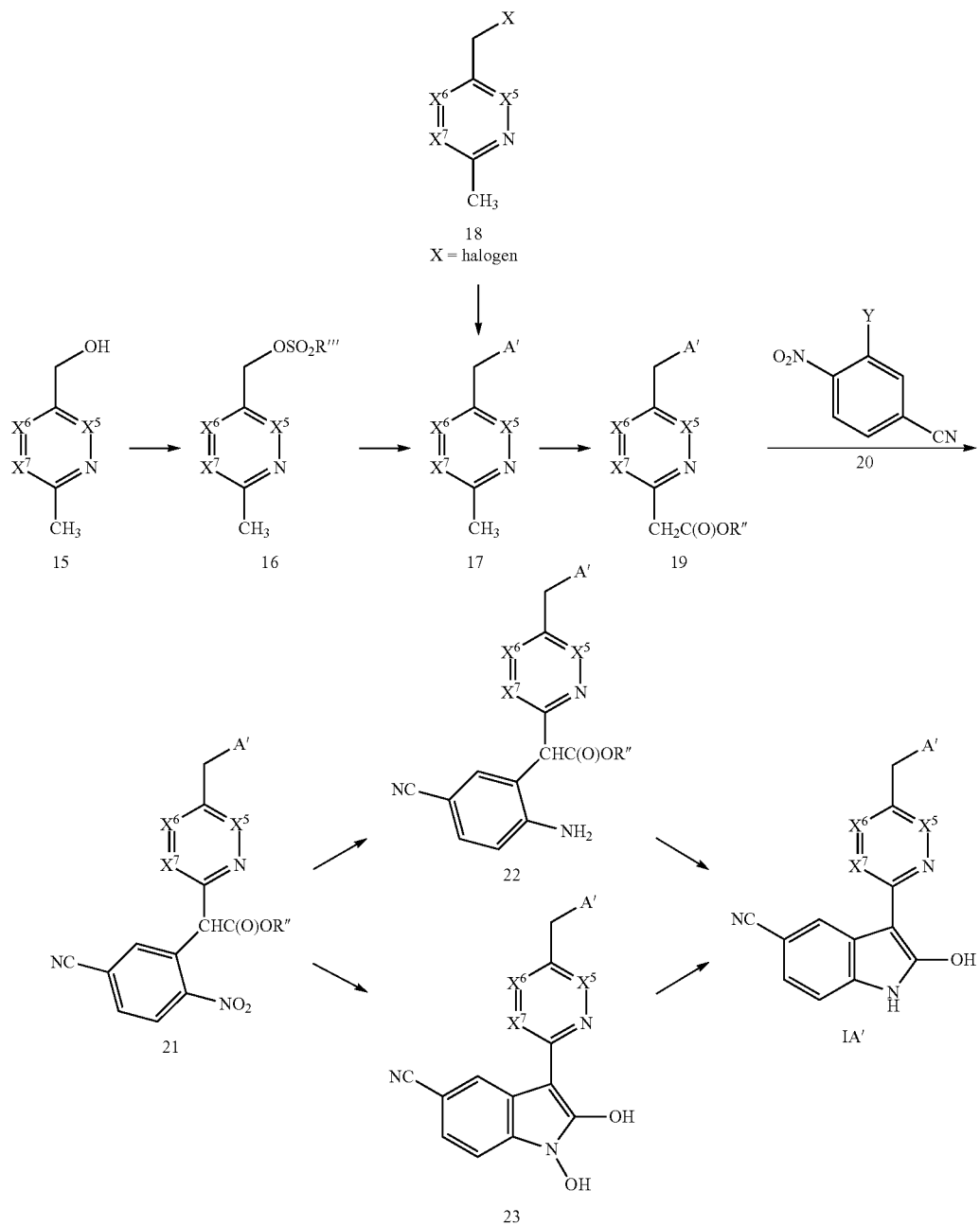

Alternatively, for preparing compounds IA/IB wherein $R^5$ is H, compound 17 can be reacted with a carbonate R″—O—C(O)—O—R″ or a dicarbonate R″—O—C(O)—O—C(O)—O—R″, wherein R″ is $C_1$-$C_4$-alkyl or phenyl-$C_1$-$C_4$-alkyl, in the presence of a base to yield 19. This is then reacted with the benzonitrile 20, in which Y is H or halogen, in the presence of a base to give 21. Reduction of the nitro group yields 22, which is subjected to a cyclization reaction in the presence of an acid or a base. Alternatively, 21 can be treated with suitable reduction agent to yield 23, which is then reduced to IA'. Compound 17 can be prepared by reacting 15 with a sulfonylhalide R‴$SO_2$X, where R‴ is $C_1$-$C_4$-alkyl, $C_1$-$C_4$-haloalkyl, phenyl, halophenyl, nitrophenyl or benzyl and X is halogen, in particular Cl, to yield 16 which is then reacted with H-A', suitably in the presence of a base. 17 can also be prepared by first reacting 18 with a compound H-A', suitably in the presence of a base, and then with a methylmagnesium halide in the presence of iron-(2,4-pentanedionate).

Compounds IA and IB wherein two radicals $R^4$ of groups $X^6$ and $X^7$, together with the carbon atoms to which they are bound, form a phenyl ring, or wherein $R^5$ and a radical $R^4$ of the group $X^6$, together with the carbon atoms to which they are bound, form a phenyl ring, can be prepared by reacting a compound 24 or a compound 25 with 1 in analogy to the reaction of 1 and 7 described in scheme 2.

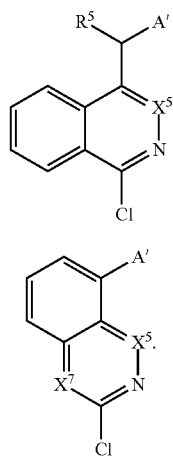

Compounds IA' in which A' is different from A by having at least one nitrogen ring atom carrying a protective group can be deprotected by known methods to yield compounds IA.

In general, the starting compounds 1 are commercially available or can be prepared via customary methods.

Compounds IA can be converted into compounds IB, wherein $R^2$ is fluorine, by reaction of IA with a suitable fluorinating agent, such as 1-fluoro-2,4,6-trimethylpyridinium triflate in the presence of a suitable base, such as n-butyllithium or sodium bis(trimethylsilyl)amide in a suitable solvent, such as tetrahydrofuran or dioxane at from −40° C. to 80° C.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", AndréLoupy (Ed.), Wiley-VCH 2002.

The acid addition salts of compounds IA and IB are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The present invention further relates to a pharmaceutical composition comprising at least one compound of formulae IA or IB, a stereoisomer, prodrug, tautomer and/or physiologically tolerated acid addition salt thereof and optionally at least one physiologically acceptable carrier and/or auxiliary substance.

The invention also relates to the use of the compounds of formulae IA or IB or of a stereoisomer, prodrug, tautomer or physiologically tolerated acid addition salt thereof for the preparation of a medicament for the treatment of a disorder susceptible to the treatment with a compound that modulates, preferably inhibits, the activity of glycogen synthase kinase 3β.

Furthermore, the invention relates to a method for treating a medical disorder susceptible to treatment with a compound that modulates glycogen synthase kinase 3β activity, said method comprising administering an effective amount of at least one compound of formulae IA or IB or of a stereoisomer, prodrug, tautomer or physiologically tolerated acid addition salt thereof or of a pharmaceutical composition as defined above to a subject in need thereof.

The compounds of the of formulae IA or IB according to the present invention, as well as the stereoisomers, the tautomers, the prodrugs and physiologically tolerated acid addition salts thereof, are capable of modulating the activity on glycogen synthase kinase 3β. In particular, the compounds of the of formulae IA or IB, as well as the stereoisomers, the tautomers, the prodrugs and physiologically tolerated acid addition salts thereof, have an inhibitory activity on glycogen synthase kinase 3β. Amongst the compounds of formulae IA or IB those are preferred which achieve effective inhibition at low concentrations. In particular, compounds of the formulae IA and IB are preferred which inhibit glycogen synthase kinase 3β at a level of $IC_{50}$<1 μMol, more preferably at a level of $IC_{50}$<0.5 μMol, particularly preferably at a level of $IC_{50}$<0.2 μMol and most preferably at a level of $IC_{50}$<0.1 μMol.

Therefore the compounds of the of formulae IA or IB according to the present invention, their stereoisomers, tautomers, their prodrugs and their physiologically tolerated acid addition salts are useful for the treatment of a medical disorder susceptible to treatment with a compound that modulates glycogen synthase kinase 3β activity. As mentioned above, diseases caused by abnormal GSK-3β activity and which thus can be treated by supplying the compound of the formulae IA and IB, a steroisomer, tautomer, prodrug and/or a physiologically tolerated acid addition salt thereof, include in particular neurodegenerative diseases such as Alzheimer's disease. In addition, the compounds of the present invention are also useful for treatment of other neurodegenerative diseases such as Parkinson's disease, tauopathies (e.g. frontotemporoparietal dementia, corticobasal degeneration, Pick's disease, progressive supranuclear palsy, argyophilic brain disease) and other dementia including vascular dementia; acute stroke and others traumatic injuries; cerebrovascular accidents (e.g. age related macular degeneration); brain and spinal cord trauma; peripheral neuropathies;

bipolar disorders, retinopathies and glaucoma. In addition, the compounds of the present invention are also useful for treatment of schizophrenia.

Diseases which can be treated by supplying the compound of the of formulae IA or IB, a steroisomer, tautomer, prodrug and/or a physiologically tolerated acid addition salt thereof, include furthermore inflammatory diseases, such as rheumatoid arthritis and osteoarthritis.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the compounds of the formulae IA or IB involves a method. In this method, an effective quantity of one or more compounds IA or IB, a steroisomer, tautomer, prodrug or physiologically tolerable acid addition salt thereof, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to pharmaceutical compositions for treating an individual, preferably a mammal, in particular a human being, productive animal or domestic animal. Thus, the compounds according to the invention are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the pharmaceutical compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; ° pacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

EXAMPLES

The compounds were either characterized via proton-NMR in d$_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s, br.), doublet (d), broad doublet (d br.), triplet (t), broad triplet (t br.), quartet (q), quintet (quint.) and multiplet (m).

Abbreviations:

| | |
|---|---|
| DMSO | dimethylsulfoxide |
| DCM | dichloromethane |
| DMF | dimethylformamide |
| MeOH | methanol |
| TMSI | trimethylsilyliodide |
| TFA | trifluoroacetate |
| TLC | thin layer chromatography |
| RT | room temperature |
| d | days |

I. Preparation Examples

Example 1

3-(5-((Dihydro-1H-furo[3,4-c]pyrrol-5(3H,6H,6aH)-yl)methyl)pyridin-2-yl)-2-hydroxy-1H-indole-5-carbonitrile

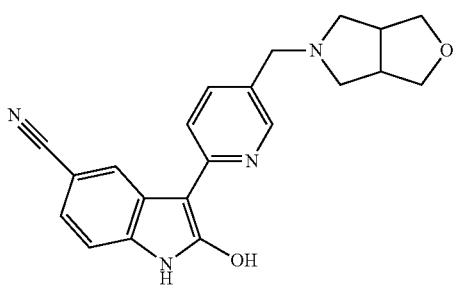

1.1 6-Chloro-N-methoxy-N-methylnicotinamide

A suspension of 2.3 g (12.81 mmol) of 6-chloronicotinoyl chloride and 1.53 g (15.37 mmol) of N,O-dimethylhydroxylamine in 46 mL of dichloromethane was cooled to 0° C. After dropwise addition of 5.36 mL (38.4 mmol) of triethylamine the resulting reaction mixture was warmed to RT and stirred for further 16 h. The mixture was subsequently washed with water (40 mL), 5% citric acid (40 mL), water (40 mL), and brine (40 mL). The organic layer was dried with $Na_2SO_4$, filtered, and the solvent was evaporated at reduced pressure yielding the titled compound as an oil. Amount 2.30 g. Yield 89%.

$^1$H-NMR (CDCl$_3$, 400 MHz) δ 3.42 (s, 3H), 3.59 (s, 3H), 7.41 (dd, 1H), 8.04 (dd, 1H), 8.79 (d, 1H)

MS (ES-API) m/z 201.0 (M+H$^+$, 100%).

1.2 6-(5-Cyano-2-hydroxy-1H-indol-3-yl)-N-methoxy-N-methylnicotin-amide

To a solution of 473 mg (2.99 mmol) of 2-oxoindoline-5-carbonitrile in DMF (10 mL) were added 229 mg (5.73 mmol) of sodium hydride (60% on mineral oil) as a solid. After stirring the resulting suspension for 60 min at RT, a solution of 500 mg (2.49 mmol) of 6-chloro-N-methoxy-N-methylnicotinamide from example 1.1 in DMF (10 mL) was added slowly and the mixture was stirred for 80 min at 120° C. The reaction was cooled down to RT and a saturated solution of NH$_4$CL (40 mL) was added and the resulting precipitate was collected by filtration. The precipitate was washed with water and hexane and afterwards dried in a vacuum oven. Yellow solid. Amount 265 mg. Yield 33%.

$^1$H-NMR (DMSO-d$_6$, 400 MHz) δ 3.30 (s, 3H), 3.69 (s, 3H), 7.04 (d, 1H), 7.81 (d, 1H), 7.98 (s, 1H), 8.02 (d, 1H), 8.69 (s, 1H), 11.0 (s, 1H)

MS (ES-API Pos.) m/z 323.1 (M+H$^+$, 100%), MS (ES-API Neg.) m/z 321.1 ([M–H]$^+$, 100%).

1.3 3-(5-Formylpyridin-2-yl)-2-hydroxy-1H-indole-5-carbonitrile

To an icecold suspension of 50 mg (0.16 mmol) of 6-(5-cyano-2-hydroxy-1H-indol-3-yl)-N-methoxy-N-methylnicotin-amide from example 1.2 in THF (4 mL) were added 19.4 mg (0.51 mmol) of LiAlH$_4$ as a solid in small portions. The resulting mixture was stirred at that temperature for further 30 min. After diluting with ethyl acetate the reaction was quenched by adding 4.2 mL of a 0.35 M solution of KHSO$_4$. The resulting solution was stirred for further 60 min, the phases were separated, and the precipitate in the organic layer was collected by filtration, washed with water and ethyl acetate, and dried in a vacuum oven yielding a red solid. Amount 28 mg. Yield 68%.

$^1$H-NMR (DMSO-d$_6$, 400 MHz) δ 7.06 (d, 1H), 7.44 (d, 1H), 7.85 (d, 1H), 7.93 (d, 1H), 8.06 (s, 1H), 8.70 (s, 1H), 9.72 (s, 1H), 11.13 (s, 1H), 14.52 (bs, 1H); MS.

1.4 3-(5-((Dihydro-1H-furo[3,4-c]pyrrol-5(3H,6H,6aH)-yl)methyl)pyridin-2-yl)-2-hydroxy-1H-indole-5-carbonitrile 164 mg of 3-(5-Formylpyridin-2-yl)-2-hydroxy-1H-indole-5-carbonitrile (0.62 mmol) from example 1.3 were dissolved in DMSO at 50° C. To this solution 134 mg (1.18 mmol) of hexahydro-1H-furo[3,4-c]pyrrole were added and the resulting deep-red solution was stirred at this temperature for 90 min. Afterwards 263 mg (1.24 mmol) of sodium triacetoxyborohydride were added and the mixture was stirred for 4 h and then cooled to RT followed by further stirring for 16 h. The reaction mixture was diluted with ethyl acetate (20 mL) and washed with sat. NaHCO$_3$ solution. The aqueous phase was re-extracted with ethyl acetate and the combined organic phases were washed with brine (5×), dried over Na$_2$SO$_4$, filtered, and evaporated under reduced pressure. The crude was purified by flash chromatography (silica gel, DCM/MeOH) yielding a yellow solid. Amount 95 mg. Yield 42%.

$^1$H-NMR (DMSO-d$_6$, 400 MHz) δ 2.40 (dd, 2H), 2.55 (m, 2H), 2.72 (m, 2H), 3.47 (s, 2H), 3.74 (m, 2H), 7.01 (dd, 1H), 7.28 (dd, 1H), 7.79 (d, 1H), 7.84 (d, 1H), 7.91 (s, 1H), 8.11 (s, 1H), 10.85 (s, 1H)

MS (ES-API Pos.) m/z 361.1 (M+H$^+$, 100%), MS (ES-API Neg.) m/z 359.1 ([M–H]$^-$, 100%).

Example 2

3-(5-(Morpholinomethyl)-pyridin-2-yl)-1H-pyrrolo[2,3-b]pyridin-2-ol

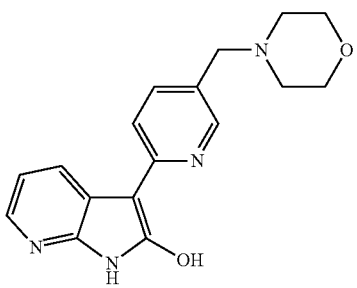

2.1 2-Chloro-5-(chloromethyl)-pyridine 1-oxide

To an icecold solution of 2-chloro-5-(chloromethyl)-pyridine (5 g, 29.6 mmol) in DCM (130 mL) was added dropwise a solution of 3-chlorobenzo-peroxoic acid (10.23 g, 59.3 mmol) in DCM (80 mL). The resulting solution was warmed to RT and stirred for 7 d till all starting material was consumed as judged by TLC. After this the reaction mixture was carefully treated with a saturated $K_2CO_3$ solution. The resulting precipitate was removed by filtration and the organic layer was washed with a saturated $K_2CO_3$ solution and brine. The organic layer was dried, filtered, and evaporated yielding the titled compound as an oil which slowly crystallizes (5.3 g, 90% yield).

$^1$H-NMR (CDCl$_3$, 400 MHz) δ 4.52 (s, 2H), 7.26 (dd, 1H), 7.52 (d, 11-1), 8.42 (d, 1H)

MS (ES-API Pos) m/z 178.0 (M+H$^+$, 100%).

2.2 2-Chloro-5-(morpholinomethyl)-pyridine 1-oxide

A mixture of 1.5 g (8.43 mmol) of 2-chloro-5-(chloromethyl)pyridine 1-oxide from example 2.1, morpholine (1.474 ml, 16.85 mmol), and potassium carbonate (1.17 g, 8.43 mmol) in acetonitrile (17 ml) was stirred at ambient temperature overnight then concentrated in vacuo. The residue was purified by flash chromatography (silica gel, DCM/MeOH) yielding a brown oil. Amount 1.23 g. Yield 64%.

$^1$H-NMR (CDCl$_3$, 400 MHz) δ 2.49 (m, 4H), 3.48 (s, 2H), 3.74 (m, 2H), 7.22 (dd, 1H), 7.46 (d, 1H), 8.42 (d, 1H)

MS (ES-API Pos) m/z 229.1 (M+H$^+$, 100%).

2.3 3-(5-(Morpholinomethyl)-pyridin-2-yl)-1H-pyrrolo[2,3-b]pyridin-2-ol

To a solution of 352 mg (2.62 mmol) of 1H-pyrrolo[2,3-b]pyridin-2(3H)-one in DMF (7 mL) was added sodium hydride on mineral oil (210 mg, 5.25 mmol) in small portions. The resulting suspension was stirred for 60 min at ambient temperature. Then a solution of 500 mg (2.187 mmol) of 2-chloro-5-(morpholinomethyl)-pyridine 1-oxide from example 2.2 dissolved in DMF (7 mL) was added dropwise and the mixture was stirred for 30 min at 100° C. The solution was cooled down to RT and was partitioned between a 2M aqueous HCl solution (60 mL) and ethyl acetate (40 mL). The aqueous layer was then carefully saturated by the addition of solid NaHCO$_3$ and then extracted with ethyl acetate (2×60 mL). The last two organic layers were combined and dried over MgSO$_4$, filtered, and concentrated. The crude intermediate (263 mg) was dissolved in ethyl acetate (20 mL) and 281 μL of phosphorus trichloride (3.22 mmol) were added. After stirring the resulting suspension at ambient temperature for 2 days the precipitate was removed by filtration, washed with ethyl acetate, and dissolved in water. The aqueous layer was basified by addition of NaHCO$_3$ and extracted with ethyl acetate (6×). The combined organic phases were dried over Na$_2$SO$_4$, filtered, and concentrated under reduced pressure. The crude was further purified by flash chromatography (silica gel, DCM/MeOH) yielding a yellow solid. Amount 36 mg. Yield 14%.

$^1$H-NMR (CDCl$_3$, 400 MHz) δ 2.5 (m, 4H), 3.41 (s, 2H), 3.75 (m, 4H), 6.98 (dd, 1H), 7.44 (d, 1H), 7.60 (dd, 1H), 7.69 (m, 2H), 8.00 (dd, 1H), 9.17 (bs, 1H), 14.8 (bs, 1H) MS (ES-API Pos.) m/z 311.1 (100%), (ES-API Neg.) m/z 309.1 (100%).

Example 3

3-(5-(Morpholinomethyl)-pyridin-2-yl)-1H-pyrrolo[2,3-c]pyridin-2-ol

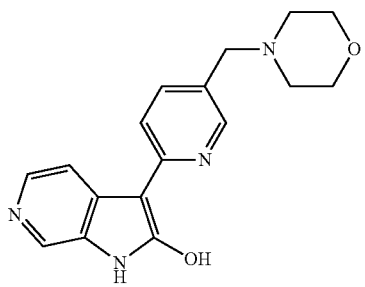

Prepared as described in examples 2.2 and 2.3 starting from 352 mg (2.62 mmol) of 1H-pyrrolo[2,3-c]pyridin-2(3H)-one and 500 mg (2.19 mmol of 2-chloro-5-(morpholinomethyl) pyridine 1-oxide). Amount 33 mg. Yield 14%.

$^1$H-NMR (DMSO, 400 MHz) δ 2.37 (m, 4H), 3.43 (s, 2H), 3.58 (m, 4H), 7.55 (m, 2H), 7.62 (d, 1H), 8.07 (d, 1H), 8.38 (d, 1H), 8.45 (d, 1H), 10.32 (s, 1H), 12.12 (bs, 1H)

MS (ES-API Pos.) m/z 311.1 (100%), (ES-API Neg.) m/z 309.1 (100%).

Example 4

5-Bromo-3-(5-(morpholinomethyl)-pyridin-2-yl)-1H-pyrrolo[3,2-b]pyridin-2-ol

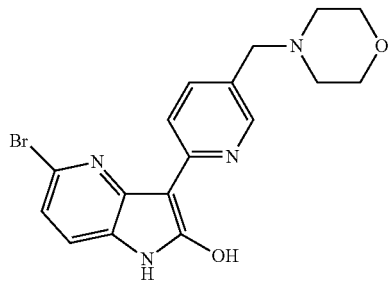

4.1 2-(5-Bromo-2-hydroxy-1H-pyrrolo[3,2-b]pyridin-3-yl)-5-(morpholinomethyl)-pyridine 1-oxide To a suspension of previously pentane-washed sodium hydride on mineral oil (75 mg, 1.88 mmol) in DMF (2 mL) was added slowly 5-bromo-1H-pyrrolo[3,2-b]pyridin-2(3H)-one (300 mg, 1.41 mmol). The resulting green solution was further stirred for 10 minutes at RT. Then a solution of 215 mg (0.939 mmol) of 2-chloro-5-(morpholinomethyl)-pyridine 1-oxide prepared like in example 2.2 in DMF was added and the resulting mixture was heated to 130° C. and stirred for further 30 min. The reaction was cooled to RT and all volatiles were removed under reduced pressure. The residue was taken up in 2 M HCl (60 mL) and washed with ethyl acetate. The aqueous layer was carefully saturated with solid NaHCO$_3$ and extracted with ethyl acetate. The combined organic phases were dried over MgSO$_4$, filtered, and evaporated yielding the titled compound as a red oil.

¹H-NMR (DMSO, 400 MHz) δ 2.44 (m, 4H), 3.55 (s, 2H), 3.62 (m, 4H), 7.14 (d, 1H), 7.34 (d, 1H), 7.88 (d, 1H), 8.41 (s, 1H), 8.80 (d, 1H), 10.62 (s, 1H)

MS (ES-API Pos.) m/z 405.0 (100%).

4.2 5-Bromo-3-(5-(morpholinomethyl)pyridin-2-yl)-1H-pyrrolo[3,2-b]pyridin-2-ol 728 mg of 2-(5-Bromo-2-hydroxy-1H-pyrrolo[3,2-b]pyridin-3-yl)-5-(morpholinomethyl)pyridine 1-oxide from example 4.1 were dissolved in ethyl acetate (20 mL) and 627 µL phosphorus trichloride (7.19 mmol) was added. After stirring the resulting suspension at ambient temperature for 2 days the precipitate was removed by filtration, washed with ethyl acetate, and dissolved in water. The aqueous layer was basified by addition of solid NaHCO₃ and extracted with ethyl acetate (6×). The combined organic phases were dried over Na₂SO₄, filtered, and concentrated under reduced pressure. The crude was further purified by flash chromatography yielding the titled compound as a yellow foam (335 mg, 48%).

¹H-NMR (DMSO, 400 MHz) δ 2.41 (m, 4H), 3.44 (s, 2H), 3.61 (m, 4H), 6.94 (d, 1H), 7.02 (d, 1H), 7.96 (d, 1H), 8.16 (s, 1H), 8.39 (d, 1H), 10.49 (bs, 1H), 14.22 (bs, 1H)

MS (ES-API Pos.) m/z 389.0 (100%).

Example 5

3-(5-(((3aS,6aS)-Hexahydropyrrolo[3,4-b]pyrrol-1(2H)-yl)methyl)-pyridin-2-yl)-2-hydroxy-1H-indole-5-carbonitrile

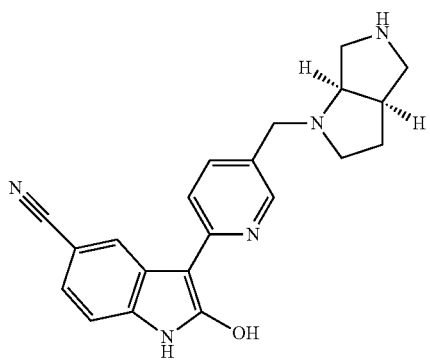

5.1 2-Chloro-5-(((3aS,6aS)-5-(ethoxycarbonyl)hexahydropyrrolo[3,4-b]pyrrol-1(2H)-yl)methyl)pyridine 1-oxide The titled compound was prepared in analogy to examples 2.2 and 2.3 using 2-chloro-5-(chloromethyl)pyridine 1-oxide (712 mg, 4 mmol), (3aS,6aS)-ethyl hexahydropyrrolo[3,4-b]pyrrole-5(1H)-carboxylate (1.1 g, 5.97 mmol), and K₂CO₃ (553 mg, 4 mmol). The obtained crude product was used without further purification in the next reaction step.

MS (ES-API Pos.) m/z 326.1 (100%).

5.2 2-(5-Cyano-2-hydroxy-1H-indol-3-yl)-5-(((3aS,6aS)-5-(ethoxy-carbonyl)hexahydropyrrolo[3,4-b]pyrrol-1(2H)-yl)methyl)pyridine 1-oxide The titled compound was prepared in analogy to example 4.1 using sodium hydride on mineral oil (101 mg, 2.53 mmol), 2-oxoindoline-5-carbonitrile (300 mg, 1.897 mmol), and 2-chloro-5-(((3aS,6aS)-5-(ethoxycarbonyl)hexahydropyrrolo[3,4-b]pyrrol-1(2H)-yl)methyl)pyridine 1-oxide (412, 1.265 mmol).

The obtained crude product was used without further purification in the next reaction step.

MS (ES-API Pos.) m/z 448.2 (100%).

5.3 (3aS,6aS)-Ethyl 1-((6-(5-cyano-2-hydroxy-1H-indol-3-yl)pyridin-3-yl)methyl)hexahydropyrrolo[3,4-b]pyrrole-5(1H)-carboxylate The titled compound was prepared in analogy to example 4.2 starting from 2-(5-cyano-2-hydroxy-1H-indol-3-yl)-5-(((3aS,6aS)-5-(ethoxy-carbonyl)hexahydropyrrolo[3,4-b]pyrrol-1(2H)-yl)methyl)pyridine 1-oxide (100 mg) and phosphorus trichloride (123 mg). The obtained crude product was used without further purification in the next reaction step.

MS (ES-API Pos.) m/z 432.2 (100%).

5.4 3-(5-(((3aS,6aS)-Hexahydropyrrolo[3,4-b]pyrrol-1(2H)-yl)methyl)-pyridin-2-yl)-2-hydroxy-1H-indole-5-carbonitrile The crude product obtained from the previous reaction step (65 mg) was dissolved in chloroform (1 mL) and TMSI (62 µL) was added dropwise. After stirring the resulting mixture for 1 h at reflux additional TMSI (62 µL) was added. The mixture was stirred for further 60 min and then cooled to RT. MeOH was carefully added and the mixture was stirred again for 30 min. After this the mixture was diluted with water and acidified by addition of diluted HCl. The aqueous layer was washed with ethyl acetate and then basified by addition of NaOH followed by extraction with DCM. The organic layer was evaporated and the resulting crude material was purified by preparative HPLC yielding 3.7 mg of the titled compound as TPA-salt (yield 5%).

¹H-NMR (DMSO, 400 MHz) δ 1.80 (m, 1H), 2.31 (m, 1H), 3.40 (m, 7H), 4.24 (m, 2H), 4.39 (d, 1H), 7.04 (d, 1H), 7.33 (d, 1H), 7.89 (s, 2H), 8.00 (s, 1H), 8.28 (s, 1H), 9.13 (bs, 1H), 9.55 (bs, 1H), 10.97 (s, 1H)

MS (ES-API Pos.) m/z 360.2 (100%).

II. Biological Tests

The compounds according to the invention exhibit very good affinities for GSK-3 (<1 µM, frequently <100 nM) and exhibited good selectivity against multiple kinase targets.

Methods—Biochemical hGSK-3beta Assay

Compounds were tested for their ability to inhibit human Glycogen Synthase Kinase-3 beta (hGSK-3β) to phosphorylate biotin-YRRAAVPPSPSLSRHSSPHQ(pS)EDEEE. Compounds were incubated with 0.5 µCi 33P-ATP, 10 µM ATP, 0.0125U hGSK-3β (Upstate cell signaling solutions) and 1 µM substrate (biotin-YRRAAVPPSPSLSRHSSPHQ (pS)EDEEE) in 50 mM HEPES, 10 mM MgCl₂, 100 mM Na₃VO₄, 1 mM DTT, 0.0075% Triton, 2% DMSO (total volume 50 µL) for 30 minutes at room temperature. The incubation was stopped by addition of an equal volume of 100 mM EDTA, 4M NaCl. 80 µL of this mixture was added to streptavidin-coated Flashplates (PerkinElmer). Following a wash step, 33P incorporation was quantified on a MicroBeta microplate liquid scintillation counter (PerkinElmer). IC₅₀'s were determined by fitting a sigmoidal dose-response curve to the counts obtained at the different concentrations in GraphPad Prism.

Methods—R-Catenin Reporter-Gene Assay

Compounds were tested for their ability to modulate β-catenin-modulated gene transcription in a LEF/TCF (T-cell factor) reporter gene assay. SY-SY5Y human neuroblastoma cells were transiently transfected with 80 ng/well TOP-FLASH plasmid (Upstate cell signaling solutions) containing two sets of three copies of the TCF binding site upstream of the Thymidine Kinase minimal promoter and firefly Luciferase open reading frame or with 80 ng/well FOP-FLASH plasmid (Upstate cell signaling solutions) containing three copies of a mutated TCF binding site upstream of the Thymidine Kinase minimal promoter and firefly Luciferase open reading frame. In addition all cells were transiently transfected with the 20 ng/well pRL-TK plasmid (Promega) containing the herpes simplex virus thymidine kinase promoter to provide low to moderate levels of *Renilla Luciferase* expression. Transfection medium was exchanged for serum-free medium containing the test substance and incubated for 24 h at 37 degreed C. The incubation was stopped and quantified using the Dual Glo Luciferase Assay (Promega) as indicated and quantified on a Pherastar reader (BMG).

Firefly Luciferase activity was normalised for Renilla Luciferase activity per well. Subsequently, the normalised TOPFLASH response was compared to the normalised FOP-FLASH response, thus giving the LEF/TCF specific signal. The maximal response is the maximal ratio between the normalised TOPFLASH and FOPFLASH signals. Sigmoidal dose-response curves were fitted using Graphpad Prism.

The results of the binding tests are given in the table below.

| Example | GSK-3β IC$_{50}$ |
|---------|------------------|
| 1 | +++ |
| 2 | + |
| 3 | ++ |
| 4.1 | ++ |
| 4 | +++ |
| 5 | +++ |

GSK-3β IC$_{50}$:
Ranges:
+++ IC$_{50}$ nM
++ 100 nM < IC$_{50}$ < 10 μM
+ 10 μM < IC$_{50}$ < 100 μM

We claim:
1. Heterocyclic compounds of the general formulae IA

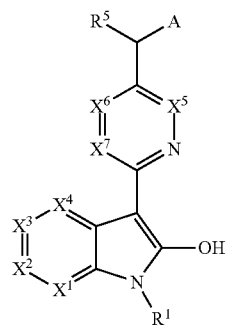

(IA)

the stereoisomers, N-oxides or physiologically tolerated acid addition salts thereof, wherein
A is a 6-, 7-, 8-, 9-, 10-, 11-, 12-, 13- or 14-membered bicyclic or tricyclic saturated N-bound heterocyclic ring containing one nitrogen atom and optionally 1, 2 or 3 further heteroatoms or heteroatom-containing groups selected from N, O, S, SO and SO$_2$ as ring members and optionally carrying 1, 2, 3 or 4 substituents R$^6$;

$X^1$, $X^2$, $X^3$ and $X^4$ are independently of each other selected from the group consisting of CR$^3$ and N;

$X^5$, $X^6$ and $X^7$ are independently of each other selected from the group consisting of CR$^4$ and N;

with the proviso that at most one of $X^5$, $X^6$ and $X^7$ is N;

R$^1$ is hydrogen or a hydrolysable group;

each R$^3$ is independently selected from the group consisting of hydrogen, CN, NR$^a$R$^b$, OH, halogen, C$_1$-C$_6$-alkyl, C$_1$-C$_6$-haloalkyl, C$_3$-C$_7$-cycloalkyl, C$_3$-C$_7$-halocycloalkyl, C$_2$-C$_4$-alkenyl, C$_2$-C$_4$-haloalkenyl, C$_1$-C$_6$-alkoxy, C$_1$-C$_6$-haloalkoxy, formyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, C$_1$-C$_6$-alkyl-NR$^a$R$^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals R$^7$ and wherein Ar may also be bonded via a CH$_2$ group;

each R$^4$ is independently selected from the group consisting of hydrogen, CN, NR$^a$R$^b$, OH, halogen, C$_1$-C$_6$-alkyl, C$_1$-C$_6$-haloalkyl, C$_3$-C$_7$-cycloalkyl, C$_3$-C$_7$-halocycloalkyl, C$_2$-C$_4$-alkenyl, C$_2$-C$_4$-haloalkenyl, C$_1$-C$_6$-alkoxy, C$_1$-C$_6$-haloalkoxy, formyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, C$_1$-C$_6$-alkyl-NR$^a$R$^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals R$^7$ and wherein Ar may also be bonded via a CH$_2$ group; or in case $X^6$ and $X^7$ are both CR$^4$, then the two radicals R$^4$ of these groups $X^6$ and $X^7$, together with the carbon atoms to which they are bound, may also form together a phenyl ring;

R$^5$ is hydrogen; or
in case $X^6$ is CR$^4$, then R$^4$ of this group $X^6$ and R$^5$, together with the carbon atoms to which they are bound, may also form together a phenyl ring;

each R$^6$ is independently selected from the group consisting of C$_1$-C$_4$-alkyl and C$_1$-C$_4$-haloalkyl;

each R$^7$ is independently selected from the group consisting of halogen, CN, C$_1$-C$_6$-alkyl, C$_1$-C$_6$-haloalkyl, C$_3$-C$_6$-cycloalkyl, C$_3$-C$_6$-halocycloalkyl, C$_1$-C$_6$-alkoxy, C$_1$-C$_6$-haloalkoxy, NR$^a$R$^b$, a phenyl group and an aromatic 5- or 6-membered C-bound heteroaromatic radical comprising one nitrogen atom and optionally 1, 2 or 3 further heteroatoms independently selected from O, S and N as ring members, wherein phenyl and the heteroaromatic radical are, independently of each other, unsubstituted or substituted by 1, 2, 3 or 4 radicals selected from halogen, cyano, C$_1$-C$_4$-alkyl, C$_1$-C$_4$haloalkyl, C$_1$-C$_4$alkoxy and C$_1$-C$_4$haloalkoxy; and R$^a$ and R$^b$ are independently of each other selected from the group consisting of hydrogen, C$_1$-C$_6$-alkyl, C$_1$-C$_4$haloalkyl, C$_1$-C$_4$alkoxy, C$_1$-C$_4$haloalkoxy, C$_1$-C$_4$alkylcarbonyl and C$_1$-C$_4$-haloalkylcarbonyl; or $R^a$ and $R^b$ form, together with the nitrogen atom to which they are bonded, a 3-, 4-, 5-, 6- or 7-membered saturated or unsaturated aromatic or non-aromatic N-heterocyclic ring, which may contain 1 further heteroatom or heteroatom-containing group selected from N, O, S, SO and $SO_2$ as a ring member.

2. The heterocyclic compounds of claim 1, wherein A is a bi- or tricyclic saturated N-bound heterocyclic ring and either all of $X^1$, $X^2$, $X^3$ and $X^4$ are $CR^3$ or one of $X^1$, $X^2$, $X^3$ and $X^4$ is N and the other three are $CR^3$.

3. The heterocyclic compounds of claim 1, wherein A is a bicyclic saturated N-bound heterocyclic ring.

4. The heterocyclic compounds of claim 3, wherein A is a 7-, 8-, 9- or 10-membered bicyclic saturated N-bound heterocyclic ring.

5. The heterocyclic compounds of claim 4, wherein A is a 7-, 8-, 9- or 10-membered bicyclic saturated N-bound heterocyclic ring containing one nitrogen atom and 1 further heteroatom selected from O and N as ring members.

6. The heterocyclic compounds of claim 5, wherein the bicyclic ring A is selected from one of the following formulae:

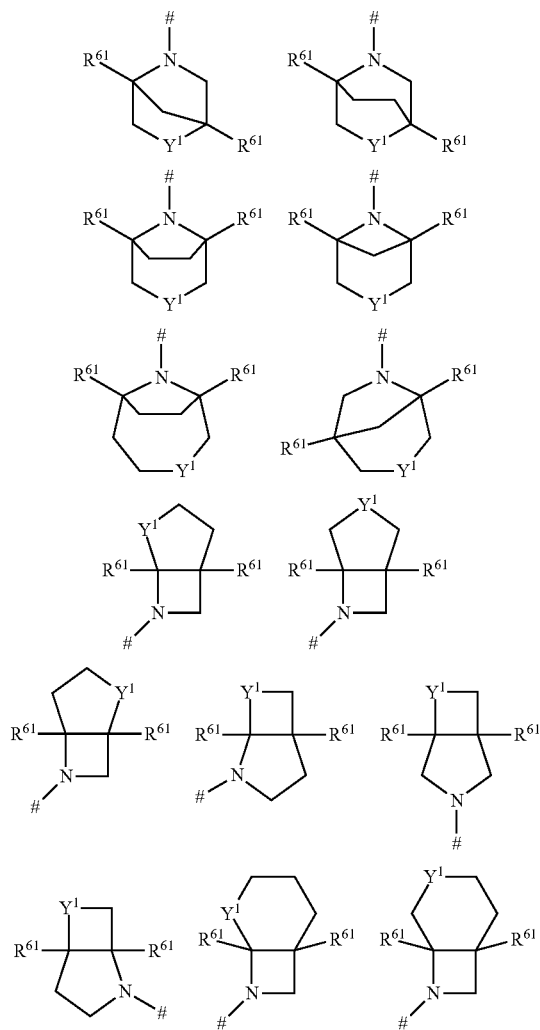

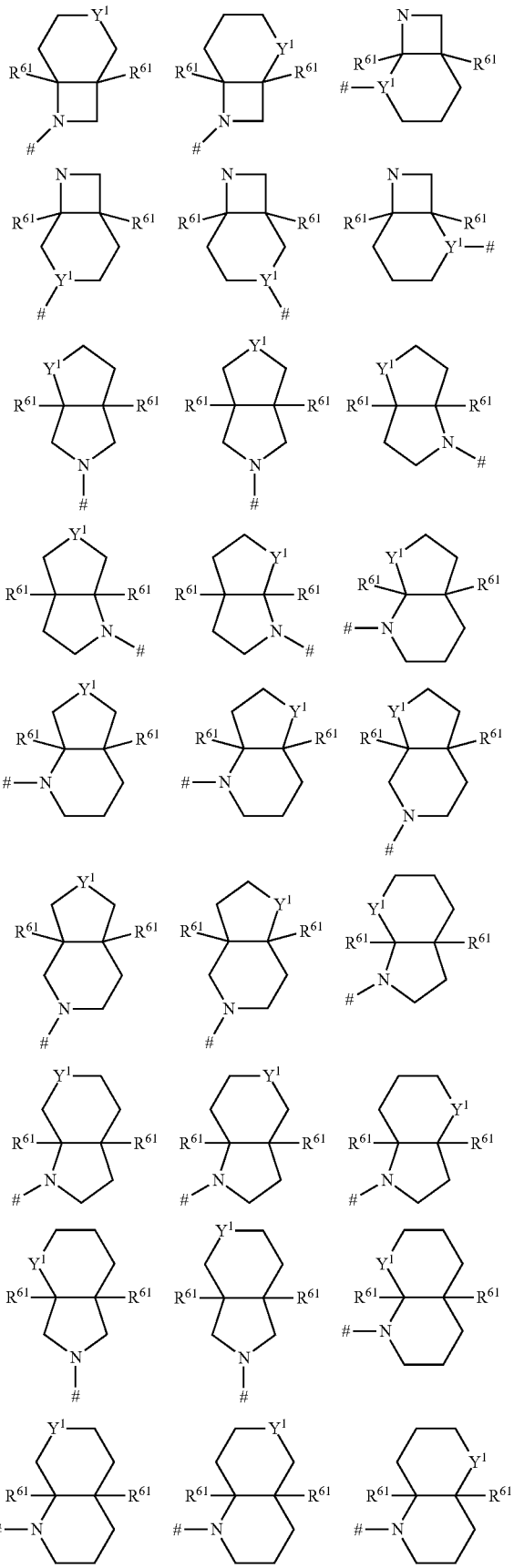

-continued

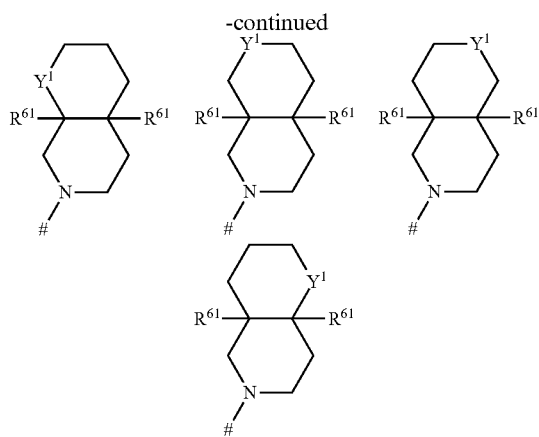

and the stereoisomers thereof;
where
Y$^1$ is O or NR$^{61}$;
each R$^{61}$, independently of its occurrence, is hydrogen or has one of the meanings given in claim 1 for R$^6$; and
# is the attachment point to the remainder of the molecule.

7. The heterocyclic compounds of claim 6, wherein A is selected from one of the following formulae:

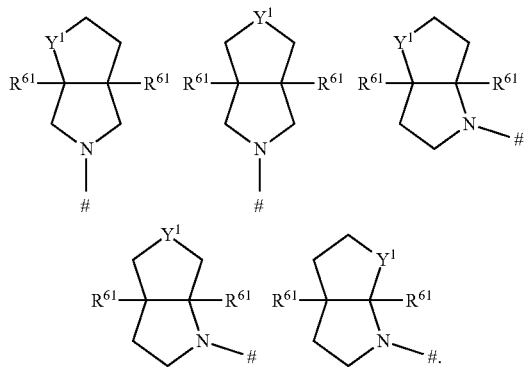

8. The heterocyclic compounds of claim 6, wherein R$^{61}$ is hydrogen.

9. The heterocyclic compounds of claim 1, wherein X$^7$ is CR$^4$.

10. The heterocyclic compounds of claim 1, wherein X$^5$, X$^6$ and X$^7$ are CR$^4$.

11. The heterocyclic compounds of claim 1, wherein R$^1$ is hydrogen.

12. The heterocyclic compounds of claim 1, wherein each R$^3$ is independently selected from hydrogen, halogen, CN, $C_1$-$C_6$-alkyl, $C_1$-$C_6$-haloalkyl, $C_1$-$C_6$-alkoxy and $C_1$-$C_6$-haloalkoxy.

13. The heterocyclic compounds of claim 12, wherein R$^3$ is hydrogen, halogen or cyano.

14. The heterocyclic compounds of claim 1, wherein each R$^4$ is independently selected from hydrogen, halogen, CN, $C_1$-$C_6$-alkyl, $C_1$-$C_6$-haloalkyl, $C_1$-$C_6$-alkoxy and $C_1$-$C_6$-haloalkoxy.

15. The heterocyclic compounds of claim 1, wherein R$^4$ is hydrogen.

16. The heterocyclic compounds of claim 1, wherein R$^5$ is hydrogen.

17. A pharmaceutical composition comprising at least one heterocyclic compound of claim 1, a stereoisomer, N-oxide or physiologically tolerated acid addition salt thereof and at least one physiologically acceptable carrier or auxiliary substance.

18. A method for treating a neurodegenerative disorder or an inflammatory disorder comprising administering to a subject in need thereof an effective amount of at least one heterocyclic compound as defined in claim 1 or of a stereoisomer, N-oxide or physiologically tolerated acid addition salt thereof, wherein the disorder is selected from the group consisting of schizophrenia, Alzheimer's disease, Parkinson's disease, tauopathies, vascular dementia, peripheral neuropathies, bipolar disorders, retinopathies, glaucoma, rheumatoid arthritis, and osteoarthritis.

19. The heterocyclic compounds of claim 1, selected from the group consisting of:
 3-(5-((dihydro-1H-furo[3,4-c]pyrrol-5(3H,6H,6aH)-yl) methyl)pyridin-2-yl)-2-hydroxy-1H-indole-5-carbonitrile; and
 3-(5-(((3aS,6aS)-hexahydropyrrolo[3,4-b]pyrrol-1(2H)-yl)methyl)-pyridin-2-yl)-2-hydroxy-1H-indole-5-carbonitrile.

* * * * *